US008026064B2

(12) United States Patent
DeNise et al.

(10) Patent No.: US 8,026,064 B2
(45) Date of Patent: *Sep. 27, 2011

(54) COMPOSITIONS, METHODS AND SYSTEMS FOR INFERRING BOVINE BREED

(75) Inventors: Sue K. DeNise, Davis, CA (US); Paul Charteris, Davis, CA (US); David Rosenfeld, Sacramento, CA (US); Tom Holm, Salt Lake City, UT (US); Stephen Bates, Davis, CA (US)

(73) Assignees: Metamorphix, Inc., Beltsville, MD (US); Cargill, Incorporated, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/148,507

(22) Filed: Apr. 18, 2008

(65) Prior Publication Data

US 2009/0221432 A1    Sep. 3, 2009

Related U.S. Application Data

(63) Continuation of application No. 10/750,622, filed on Dec. 31, 2003, now Pat. No. 7,511,127.

(60) Provisional application No. 60/437,482, filed on Dec. 31, 2002.

(51) Int. Cl.
*C12Q 1/68* (2006.01)

(52) U.S. Cl. ......................................................... 435/6.1

(58) Field of Classification Search .......................... None
See application file for complete search history.

(56) References Cited

U.S. PATENT DOCUMENTS

| | | | |
|---|---|---|---|
| 5,041,371 A | 8/1991 | Cowan et al. |
| 5,374,523 A | 12/1994 | Collier et al. |
| 5,374,526 A | 12/1994 | Rothschild et al. |
| 5,427,930 A | 6/1995 | Birkenmeyer et al. |
| 5,550,024 A | 8/1996 | Rothschild et al. |
| 5,582,987 A | 12/1996 | Lewin et al. |
| 5,612,179 A | 3/1997 | Simons |
| 5,614,364 A | 3/1997 | Tuggle et al. |
| 5,851,762 A | 12/1998 | Simons |
| 5,935,784 A | 8/1999 | Rothschild et al. |
| 6,077,697 A | 6/2000 | Hadlaczky et al. |
| 6,103,446 A | 8/2000 | Devlin et al. |
| 6,103,466 A | 8/2000 | Grobet et al. |
| 6,218,119 B1 | 4/2001 | Kuiper et al. |
| 6,242,191 B1 | 6/2001 | Fluharty et al. |
| 6,383,751 B1 | 5/2002 | Barendse |
| 6,410,231 B1 | 6/2002 | Arnold et al. |
| 6,458,531 B1 | 10/2002 | Rothschild et al. |
| 6,458,544 B1 | 10/2002 | Miller |
| 6,479,242 B1 | 11/2002 | Guo et al. |
| 6,627,401 B2 | 9/2003 | Ralham |
| 6,632,606 B1 | 10/2003 | Ullman |
| 6,701,869 B2 | 3/2004 | Fuqua |
| 6,770,437 B1 | 8/2004 | Taylor et al. |
| 6,803,190 B1 | 10/2004 | Rothschild et al. |
| 6,844,159 B2 | 1/2005 | Tuggle et al. |
| 6,919,177 B2 | 7/2005 | Rothschild et al. |
| 7,070,929 B2 | 7/2006 | Tuggle et al. |
| H2191 H | 6/2007 | Wang |
| 7,238,479 B2 | 7/2007 | Smith et al. |
| 7,244,564 B2 | 7/2007 | Rothschild et al. |
| H2220 H | 7/2008 | Wang |
| 7,468,248 B2 * | 12/2008 | DeNise et al. |
| 7,511,127 B2 * | 3/2009 | DeNise et al. |
| 7,537,888 B2 | 5/2009 | Georges et al. |
| 7,709,206 B2 * | 5/2010 | DeNise et al. |
| 2001/0053519 A1 | 12/2001 | Fodor et al. |
| 2002/0012934 A1 | 1/2002 | Meghen et al. |
| 2002/0069423 A1 | 6/2002 | Good et al. |
| 2002/0073440 A1 | 6/2002 | Tornell et al. |
| 2002/0094525 A1 | 7/2002 | McIntosh et al. |
| 2002/0098534 A1 | 7/2002 | McCaskey-Feazel et al. |
| 2002/0099194 A1 | 7/2002 | Efstratiadis et al. |
| 2002/0104109 A1 | 8/2002 | Bremel et al. |
| 2002/0107211 A1 | 8/2002 | Friedman et al. |
| 2002/0108136 A1 | 8/2002 | Pati et al. |
| 2002/0119442 A1 | 8/2002 | Dunlop et al. |
| 2002/0119451 A1 | 8/2002 | Usuka et al. |
| 2002/0123058 A1 | 9/2002 | Threadgill et al. |

(Continued)

FOREIGN PATENT DOCUMENTS

AU    200227460    10/2002

(Continued)

OTHER PUBLICATIONS

Kriegesmann et al. Two breed-specific bovine MC1-R alleles in Brown Swiss and Saler breeds. J. Dairy Sci. (2001) vol. 84, pp. 1768-1771.*

Klungland et al. The role of melanocyte-stimulating hormone (MSH) receptor in bovine coat color determination. Mammalian Genome (1995) vol. 6, pp. 636-639.*

Nejati-Javaremi, A., et al., Effect of Total Allelic Relationship on Accuracy of Evaluation and Response to Selection; J. Anim. Sci 1997, 75:1738-1745.

Riquet et al., "Fine-Mapping of Quantitative Trait Loci by Identity by Descent in Outbred Populations: Application to Milk Production in Dairy Cattle," Proc. Natl. Acad. Sci., Aug. 1999, 96:9252-9257.

(Continued)

*Primary Examiner* — Kenneth R. Horlick
*Assistant Examiner* — David Thomas
(74) *Attorney, Agent, or Firm* — McKeon Meuner Carlin & Curfman LLC

(57) ABSTRACT

Provided herein are methods to discover and use single nucleotide polymorphisms (SNP) for identifying breed, or line and breed, or line composition of a bovine subject. The present invention further provides specific nucleic acid sequences, SNPs, and SNP patterns that can be used for identifying breed or breed combinations for Angus, Holstein, Limousin, Brahman, Hereford, Simmental, Gelbvieh, Charolais and Beefmaster breeds. These patterns can be utilized to manage animals in a feedlot to obtain optimum performance based on known characteristics of specific breeds and identify animals for breeding in selection programs. In another aspect, these patterns can be used to ensure labeling on breed specific branded products.

26 Claims, No Drawings

U.S. PATENT DOCUMENTS

| | | |
|---|---|---|
| 2002/0129394 A1 | 9/2002 | Aso et al. |
| 2002/0137080 A1 | 9/2002 | Usuka et al. |
| 2002/0137139 A1 | 9/2002 | Byatt et al. |
| 2002/0137160 A1 | 9/2002 | Byatt et al. |
| 2002/0137701 A1 | 9/2002 | Lee et al. |
| 2002/0142315 A1 | 10/2002 | Hale et al. |
| 2002/0182622 A1 | 12/2002 | Nakamura et al. |
| 2003/0009292 A1 | 1/2003 | Mei et al. |
| 2003/0017487 A1 | 1/2003 | Xue et al. |
| 2003/0077617 A1 | 4/2003 | Kim et al. |
| 2003/0103962 A1 | 6/2003 | Campbell et al. |
| 2003/0190314 A1 | 10/2003 | Campbell et al. |
| 2003/0190619 A1 | 10/2003 | Chang et al. |
| 2003/0190644 A1 | 10/2003 | Braun et al. |
| 2003/0194730 A1 | 10/2003 | Nagaraju |
| 2003/0219819 A1 | 11/2003 | Marquess |
| 2004/0018511 A1 | 1/2004 | Cai et al. |
| 2004/0076977 A1 | 4/2004 | Georges et al. |
| 2005/0260603 A1 | 11/2005 | DeNise et al. |
| 2005/0287531 A1 | 12/2005 | DeNise et al. |
| 2006/0172329 A1 | 8/2006 | Taylor et al. |
| 2006/0211006 A1 | 9/2006 | Schenkel et al. |
| 2007/0031845 A1 | 2/2007 | DeNise et al. |
| 2007/0172848 A1 | 7/2007 | Rothschild et al. |
| 2010/0162423 A1 | 6/2010 | DeNise et al. |

FOREIGN PATENT DOCUMENTS

| | | |
|---|---|---|
| AU | 2002356998 | 8/2003 |
| AU | 2003234372 | 12/2003 |
| AU | 2003269993 | 4/2004 |
| AU | 2004204182 | 7/2004 |
| AU | 2004212103 | 8/2004 |
| AU | 2004219584 | 8/2004 |
| AU | 2003200491 | 9/2004 |
| AU | 2004253882 | 1/2005 |
| CN | 1537942 | 10/2004 |
| CN | 101405404 A | 4/2009 |
| EP | 0 566 793 A1 | 4/1992 |
| EP | 1 226 752 A1 | 7/2002 |
| EP | 1 238 584 A1 | 9/2002 |
| EP | 1 256 632 A2 | 11/2002 |
| EP | 1 059 840 B1 | 10/2003 |
| EP | 1 352 971 A2 | 10/2003 |
| FR | 2 779 153 A1 | 12/1999 |
| WO | WO 92/13102 A1 | 8/1992 |
| WO | WO 94/03641 | 2/1994 |
| WO | WO 95/12607 | 5/1995 |
| WO | WO 95/15400 A1 | 6/1995 |
| WO | WO 98/41655 | 8/1998 |
| WO | WO 98/39475 A2 | 9/1998 |
| WO | WO 98/53102 | 11/1998 |
| WO | WO 99/01576 A1 | 1/1999 |
| WO | WO 99/02667 | 1/1999 |
| WO | WO 99/06598 | 2/1999 |
| WO | WO 99/23248 | 5/1999 |
| WO | WO 99/23256 | 5/1999 |
| WO | WO 99/32661 | 7/1999 |
| WO | WO 99/40226 | 8/1999 |
| WO | WO 00/06777 | 2/2000 |
| WO | WO 00/36143 A2 | 6/2000 |
| WO | WO 00/55372 | 9/2000 |
| WO | WO 00/69882 A1 | 11/2000 |
| WO | WO 01/11088 | 2/2001 |
| WO | WO 01/21801 A1 | 3/2001 |
| WO | WO 01/27325 | 4/2001 |
| WO | WO 01/27857 | 4/2001 |
| WO | WO 01/29262 | 4/2001 |
| WO | WO 01/34840 | 5/2001 |
| WO | WO 02/38737 A2 | 5/2001 |
| WO | WO 01/67211 A2 | 9/2001 |
| WO | WO 01/75161 A2 | 10/2001 |
| WO | WO 01/77384 | 10/2001 |
| WO | WO 01/92570 A2 | 12/2001 |
| WO | WO 02/02822 A2 | 1/2002 |
| WO | WO 02/09510 A2 | 2/2002 |
| WO | WO 02/21544 A1 | 2/2002 |
| WO | WO 02/20844 | 3/2002 |
| WO | WO 02/36824 A1 | 5/2002 |
| WO | WO 02/40666 A2 | 5/2002 |
| WO | WO 02/40709 A2 | 5/2002 |
| WO | WO 02/053778 | 7/2002 |
| WO | WO 02/059374 A1 | 8/2002 |
| WO | WO 02/064749 A2 | 8/2002 |
| WO | WO 02/064820 A1 | 8/2002 |
| WO | WO 02/070709 A2 | 9/2002 |
| WO | WO 02/072871 A2 | 9/2002 |
| WO | WO 02/076190 A2 | 10/2002 |
| WO | WO 02/090569 A2 | 11/2002 |
| WO | WO 02/090589 A1 | 11/2002 |
| WO | WO 02/101022 | 12/2002 |
| WO | WO 03/076573 A2 | 9/2003 |
| WO | WO 03/076657 A2 | 9/2003 |
| WO | WO 03/081990 A2 | 10/2003 |
| WO | WO 2004/013346 A2 | 2/2004 |
| WO | WO 2004/061124 A2 | 7/2004 |
| WO | WO 2004/061125 A2 | 7/2004 |
| WO | WO 2005/078133 | 1/2005 |
| WO | WO 2005/040400 | 5/2005 |
| WO | WO 2005/045029 | 5/2005 |
| WO | WO 2005/101230 | 10/2005 |
| WO | WO 2009/009439 | 1/2009 |
| WO | WO 2009/009752 | 1/2009 |

OTHER PUBLICATIONS

Sonstegard et al., "Comparative Map Alignment of BTA27 and HSA4 and 8 to Identify Conserved Segments of Genome Containing Fat Deposition QTL", Mammalian Genome, 2000, 11:682-688.

Product #1256, Random Primer 24, *New England Biolabs Catalog*, pp. 121, Jan. 1, 1998.

AniGenics Announces Innovative R&D Alliance: New Animal Genomics Company Creates Coalition of Animal Genomics Research Institutions, *AniGenics Inc. Press Release*, pp. 1-2, Jul. 24, 2000.

Animal Genomics Company to Use First Detailed Human-Cattle Comparative Genomic Map: AniGenics Will Use Map to Develop New Production Traits for Cattle and New Human and Veterinary Drug Targets, *AniGenics Inc. Press Release*, pp. 1-2, Sep. 13, 2000.

Ax et al. New Developments in Managing the Bull, *CRC Press*, pp. 287-296, Jan. 1, 2001.

Davis et al. The Impact of Genetic Markers on Selection, *Journal of Animal Science*, vol. Iss: 76, pp. 2331-2339, Jan. 1, 1998.

Dekkers et al. The Use of Molecular Genetics in the Improvement of Agricultural Populations, *Nature*, vol. 3, pp. 22-32, Jan. 1, 2002.

Denise et al. Genetic Screening for Disease and Production, *Proc. of Western Can. Dairy Sem.—Univ. of AZ, Dept. of Animal Sci.*, pp. 1-10, Jan. 1, 1993.

Denise et al., Gene Mapping, Marker-Assisted Selection, QTLs-Boiling it Down to Cowboy Lingo, *Beef Improvement Federation Annual Meeting*, pp. 1-6, Jun. 1, 1994.

Denise et al., Genetic and Environmental Aspects of the Growth Curve Parameters in Beef Cows, *Journal of Animal Science*, vol. Iss: 61 (6), pp. 1431-1440, Jan. 1, 1985.

Denise et al., Genetic Technologies in Cow-Calf Operations—Factors Affecting Calf Crop: Biotechnology of Reproduction, *CRC Press*, pp. 177-193, Jan. 1, 2002.

Denise et al., Relationships Among Udder Shape, Udder Capacity, Cow Longevity and Calf Weights, *Journal of Animal Science*, vol. Iss: 65, pp. 366-372, Jan. 1, 1987.

Denise et al., Use of Genetic Markers in Improvement of Dairy and Beef Cattle, *Proc. of Western Can. Dairy Sem.—Univ. of AZ, Dept. of Animal Sci.*, pp. 62-69, Jan. 1, 1993.

Denise et al., Postweaning Weights and Gains of Cattle Raised Under Range and Gain Test Environments, *Journal of Animal Science*, vol. Iss: 64, pp. 969-976, Jan. 1, 1987.

Denise et al., Incorporation of Molecular Genetic Information into Genetic Prediction Models, *Proceedings of the Genetic Prediction Workshop*, pp. 1-6, Jan. 22, 1994.

Denise et al., Genetic Parameter Estimates for Postweaning Traits of Cattle in a Stressful Environment, *Journal of Animal Science*, vol. Iss: 67, pp. 2619-2626, Jan. 1, 1989

Denise, S., Biotechnology and Animal Breeding: What Can We Use Today and What Does the Future Hold?, *Great Plains and Beef Cattle Handbook*, pp. 1-4, Jan. 1, 1994.
Du et al., Heterozygosity for Genes Influencing a Quantitative Trait, *Journal of Animal Science*, vol. Iss: 80, pp. 1478-1488, Jan. 1, 2002.
Heaton et al., Selection and Use of SNP Markers for Animal Identification and Paternity Analysis in U.S. Beef Cattle, *Mammalian Genome*, vol. Iss: 13 (5), pp. 272-281, May 1, 2002.
Ioannidis et al., Replication Validity of Genetic Association Studies, *Nature Genetics*, vol. Iss: 29, pp. 306-309, Jan. 1, 2001.
Lagziel et al., Georgraphic and Breed Distribution of an Mspl PCR-RFLP in the Bovine Growth Hormone (bGH) Gene, *Animal Genetics*, vol. Iss: 31, pp. 210-213, Jan. 1, 2000.
Nollau et al., Methods for Detection of Point Mutations: Performance and Quality Assessment, *Clinical Chemistry*, vol. Iss. 43 (7), pp. 1114-1128, Jan. 1, 1997.
Pritchard et al., Inference of Population Structure Using Multilocus Genotype Data, *Genetics*, vol. Iss: 155, pp. 945-959, Jun. 1, 2000.
Rothschild, M. F., Patenting of Genetic Innovations in Animal Breeding, *7th World Congress on Genetics Applied to Livestock Production*, pp. 1-8, Aug. 19, 2002.
Tanida et al., Genetic Aspects of Longevity in Angus and Hereford Cows, *Journal of Animal Science*, vol. Iss: 66, pp. 640-647, Jan. 1, 1988.
Unanian et al., Rapid Communication: Polymerase Chain Reaction-Restricted Fragment Length Polymorphism in the Bovine Growth Hormone Gene, *Journal of Animal Science*, vol. Iss: 72, pp. 2203, Jan. 1, 1994.
Zhang et al., Molecular Genetic Markers: Nucleotide Sequence Determination of a Bovine Somatotropin Allele, *Animal Genetics*, vol. Iss: 23, pp. 578, Jan. 1, 1992.
Zhang et al., Rapid Communication: A Novel DNA Polymorphism of the Bovine Calpain Gene Detected by PCR-RFLP Analysis, *Journal of Animal Science*, vol. Iss: 74, pp. 1441, Jan. 1, 1996.
Zhang et al., Rapid Communication: Polymerase Chain Reaction-Restricted Fragment Length Polymorphism Analysis of the Bovine Somatotrophin Gene, *Journal of Animal Science*, vol. Iss: 71, pp. 2276, Jan. 1, 1993.
Zhang et al., Rapid Communication: Diallelic Single-Stranded Conformational Polymorphism Detected in the Bovine Prolactin Gene, *Journal of Animal Science*, vol. Iss: 72, pp. 256, Jan. 1, 1994.
Genometrix's High-Throughput VistaMorph Genotyping Services Selected by AniGenics to Identify Novel Traits in Livestock, *AniGenics Inc. Press Release*, pp. 1-2, Mar. 14, 2001.
Adams et al., Use of a Random Human BAC end Sequence Database for Sequence-Map Building—GenBank Accession No. AQ112913, *GenBank* Accession No. AQ112913, Jan. 1, 1998.
Akhter et al., Bos taurus Clone RP42-360C18, *GenBank* Accession No. AC092085, pp. 1-55, Jan. 1, 2002.
Ciobanu et al., Evidence of New Alleles in the Protein Kinase Adenosine Monophosphate-Activated γ3-Subunit Gene Associates with Low Glycogen Content in Pig Skeletal Muscle and Improved Meat Quality, *Genetics*, vol. Iss: 159 (3), pp. 1151-1162, Nov. 1, 2001.
Rothschild et al., The Estrogen Receptor Locus is Associated with a Major Gene Influencing Litter Size in Pigs, *Proc. Natl. Acad. Sci.*, vol. Iss: 93, pp. 201-205, Jan. 1, 1996.
Office Action Issued Against U.S. Appl. No. 12/069,845, pp. 1-19, Sep. 17, 2009.
Supplemental European Search Report, pp. 1-10, Nov. 6, 2009.
Denise, S., Whole-Genome Association Studies to Determine the Molecular Genetic Value Cattle, *AgBiotechNet Proceedings*, pp. 1-5, Jan. 1, 2003.
Gelhaus et al., Cattle MHC Genes DOA and DOB: Sequence Polymorphisms and Assignments to the Class IIb Region, *European Journal of Immunogenetics*, vol. Iss: 28, pp. 429-433, Jan. 1, 2001.
Grosse et al., Single Nucleotide Polymorphism (SNP) Discovery and Linkage Mapping of Bovine Cytokine Genes, *Mammalian Genome*, vol. Iss: 10, pp. 1062-1069, Jan. 1, 1999.
Kappes et al., A Second-Generation Linkage Map of the Bovine Genome, *Genome Research*, vol. Iss: 7, pp. 235-249, Jan. 1, 1997.

Meuwissen et al., Fine Mapping of a Quantitative Trait Locus for Twinning Rate Using Combined Linkage and Linkage Disequilibrium Mapping, *Genetics*, vol. Iss: 161, pp. 373-379, May 1, 2002.
Siler et al., Validation of Bovine SNPS from ~1X Sequencing of the Bovine Genome, *Proc. Plant and Animal Genome Meetings*, pp. 1, Jan. 1, 2003.
Stone et al., Use of Bovine EST Data and Human Genomic Sequences to Map 100 Gene-Specific Bovine Markers, *Mammalian Genome*, vol. Iss: 13, pp. 211-215, Jan. 1, 2002.
Venter et al., The Sequence of the Human Genome, *Science*, vol. Iss: 291 (5507), pp. 1304-1351, Feb. 16, 2001.
Chapman et al., Linkage Disequilibrium Mapping: The Role of Population History, Size and Structure, *Advances in Genetics*, vol. Iss: 42, pp. 413-437, Jan. 1, 2001.
Collins et al., Allelie Association with SNPs: Metrics, Populations, and the Linkage Disequilibrium Map, *Human Mutation*, vol. Iss: 17, pp. 255-262, Jan. 1, 2001.
Laegreid et al., Association of Bovine Neonatal Pc Receptor a-chain Gene (FCGRT) Haplotypes with Serum IgG Concentration in Newborn Calves, *Mammalian Genome*, vol. Iss: 13, pp. 704-710, Dec. 1, 2002.
Saito et al., Strategies for Genome-Wide Association Studies: Optimization of Study Designs by the Stepwuise Focusing Method, *Journal of Human Genetics*, vol. Iss: 47, pp. 360-365, Jan. 1, 2002.
Andersson et al. Domestic-Animal Genomics: Deciphering the Genetics of Complex Traits, *Nature*, vol. Iss: 5, pp. 202-212, Mar. 1, 2004.
Bacanu et al., The Power of Genomic Control, *American Journal of Human Genetics*, vol. Iss: 66, pp. 1933-1944, Jun. 1, 2000.
Barendse, William, Chapter 12: Development and Commercialization of a Genetic Marker for Marbling of Beef in Cattle: A Case Study, *Intellectual Property Rights in Animal Breeding and Genetics*, pp. 197-212, Jan. 1, 2002.
Baruch et al., Incorporation of Discrete Genotype Effects for Multiple Genes Into Animal Model Evaluations When Only a Small Fraction of the Population has been Genotyped, *Journal of Dairy Science*, vol. Iss: 91 (11), pp. 4365-4371, Nov. 1, 2008.
Baughman, Molly E., Office Action for U.S. Appl. No. 10/750,185, *U.S. PTO Office Action*, pp. 1-4, Jun. 14, 2006.
Baughman, Molly E., Office Action for U.S. Appl. No. 10/750,185, *U.S. PTO Office Action*, pp. 1-22, Feb. 27, 2007.
Baughman, Molly E., Office Action for U.S. Appl. No. 10/750,185, *U.S. PTO Office Action*, pp. 1-21, Dec. 12, 2007.
Baughman, Molly E., Office Action for U.S. Appl. No. 10/750,185, *U.S. PTO Office Action*, pp. 1-15, Jul. 9, 2008.
Bink et al., Marker-Assisted Prediction of Breeding Values in Dairy Cattle Populations, *Proc. 5th World Congress on Genet Applied to Livestock Prod*, vol. Iss: 21, pp. 233-236, Aug. 7, 1994.
Biswas, Amrita, Examiner's Report for AU Patent Application No. 2003303599, *AU Patent Office*, pp. 1-2, Nov. 5, 2009.
Burger, Reinhard, Linkage and the Maintenance of Heritable Variation by Mutation-Selection Balance, *Genetics*, vol. Iss: 121 (1), pp. 175-184, Jan. 1, 1989.
Calamita, Heather G., International Search Report for PCT Patent Application No. PCT/US03/41761, *International Searching Authority—US*, pp. 1-5, Jun. 21, 2006.
Calamita, Heather G., International Preliminary Examination Report for PCT Application No. PCT/US03/41766, *U.S. Searching Authority*, pp. 1-6, Jun. 21, 2006.
Calamita, Heather G., International Preliminary Examination Report for PCT Application No. PCT/US03/41761, *U.S. Searching Authority*, pp. 1-6, Jun. 21, 2006.
Carlborg et al., The Use of a Genetic Algorithm for Simultaneous Mapping of Multiple Interacting Quantitative Trait Loci, *Genetics*, vol. Iss: 155, pp. 2003-2010, Aug. 1, 2000.
Chakraborty et al., A Method to Optimize Selection on Multiple Identified Quantitative Trait Loci, *Genet Sel Evol*, vol. Iss: 34, pp. 145-170, Jan. 1, 2002.
Christie, Julie, Examiner's Report for AU Patent Application No. 2003303599, *AU Patent Office*, pp. 1-2, Sep. 19, 2008.
Christie, Julie, Examiner's Report for AU Patent Application No. 2003303599, *AU Patent Office*, pp. 1-2, Nov. 26, 2008.

Christie, Julie, Examiner's Report for AU Patent Application No. 2003303599, *AU Patent Office*, pp. 1-16, Mar. 18, 2009.
Ciobanu et al., New Alleles in Calpastatin Gene are Associated with Meat Quality Traits in Pigs, *Journal of Animal Science*, vol. Iss: 82 (10), pp. 2829-2839, Oct. 1, 2004.
Comeron et al., On the Power to Detect SNP/Phenotype Association in Candidate Quantitative Trait Loci Genome Regions: A Simulation Study, *Pacific Symposium on Biocomputing*, vol. Iss: 8, pp. 478-489, Jan. 1, 2003.
Continental Grain Company, GenomicFX: A New Venture in Animal Genetics, *ContiConnect Online*, pp. 1-3, Sep. 1, 2000.
Dani et al, Brazilian Nelore Cattle: A Melting Pot Unfolded by Molecular Genetics, *Genet Mol Res*, vol. Iss: 7 (4), pp. 1127-1137, Oct. 21, 2008.
Davis et al., SMART Breeding: Selection with Markers and Advanced Reproductive Technologies, *Proc. Assoc. Advmt. Anim. Breed. Genet.*, vol. Iss: 12, pp. 429-432, Apr. 6, 1997.
Dean et al., Comprehensive Human Genome and Amplification Using Multiple Displacement Amplification, *Proc. Natl. Acad. Sci.*, vol. Iss: 99 (8), pp. 5261-5266, Apr. 16, 2002.
Delvin et al., Genomic Control for Association Studies, *Biometrics*, vol. Iss: 55, pp. 997-1004, Dec. 1, 1999.
Douabin-Gicquel et al., Identification of 96 Single Nucleotide Polymorphisms in Eight Genes Involved in Iron Metabolism: Efficiency of Bioinformatic Extraction Compared with a Systematic Sequencing Approach, *Human Genetics*, vol. Iss: 109, pp. 393-401, Jan. 1, 2001.
Farnir et al., Extensive Genome-Wide Linkage Disequilibrium in Cattle, *Genome Research*, vol. Iss: 10, pp. 220-227, Jan. 1, 2000.
Fernando, Rohan L., Genetic Evaluation and Selection Using Genotypic, Phenotypic and Pedigree Information, *Proc. 6th World Congress on Genet Applied to Livestock Prod*, vol. Iss: 26, pp. 329-336, Jan. 1, 1998.
Flori et al., The Genome Response to Artificial Selection: A Case Study in Dairy Cattle, *PLOS One*, vol. Iss: 4 (8), pp. 1-13, Aug. 12, 2009.
Fogarty, N. M., Meat Sheep Breeding—Where We Are At and Future Challenges, *Proc. Assoc. Anim. Breed. Genet.*, vol. Iss: 18, pp. 414-421, Sep. 28, 2009.
Fredman, Jeffrey, Office Action for U.S. Appl. No. 10/750,622, *U.S. PTO Office Action*, pp. 1-8, Oct. 3, 2006.
Fredman, Jeffrey, Office Action for U.S. Appl. No. 10/750,623, *U.S. PTO Office Action*, pp. 1-5, Sep. 28, 2006.
Goddard et al., Characteristics of Genetic Markers and Maps for Cost-Effective Genome Screens Using Diallelic Markers, *Genetic Epidemiology*, vol. Iss: 22, pp. 205-220, Jan. 1, 2002.
Goddard, M.E., Gene Based Models for Genetic Evaluation—An Alternative to BLUP? *Proc. 6th World Congress on Genet Applied to Livestock Prod*, vol. Iss: 26, pp. 33-36, Jan. 1, 1998.
Gu et al., Designing an Optimum Genetic Association Study Using Dense SNP Markers and Family-Based Sample, *Front Biosci.*, vol. Iss: 8, pp. s69-80, Jan. 1, 2003.
Gu et al., Evidence of Multiple Causal Sites Affecting Weight in the IGF2-INS-TH Region of Human Chromosome 11, *Human Genetics*, vol. Iss: 110, pp. 173-181, Jan. 1, 2002.
Gurd, Scott, Office Action for CA Patent Application No. 2,512,110, *CA Patent Office*, pp. 1-3, Jul. 27, 2010.
Hackett et al., A Phylogenomic Study of Birds Reveals Their Evolutionary History, *Science*, vol. Iss: 320, pp. 1763-1768, Jun. 27, 2008.
Haley et al., Strategies to Utilize Marker-Quantitative Trait Loci Associations, *Journal of Dairy Science*, vol. Iss: 81 (2), pp. 85-97, Jan. 1, 1998.
Hayes et al., The Distribution of the Effects of Genes Affecting Quantitative Traits in Livestock, *Genet Sel Evol*, vol. Iss: 33, pp. 209-229, Jan. 1, 2001.
Hillel et al., DNA Fingerprints Applied to Gene Introgression in Breeding Programs, *Genetics*, vol. Iss: 124, pp. 783-789, Mar. 1, 1990.
Hoeschele, Ina, Elimination of Quantitative Trait Loci Equations in an Animal Model Incorporating Genetic Marker Data, *Journal of Dairy Science*, vol. Iss: 76, pp. 1693-1713, Jan. 1, 1993.
Houston et al., A Polymorphism in the 5'-Untranslated Region of the Porcine Cholecystokinin Type A Receptor Gene Affects Feed Intake and Growth, *Genetics*, vol. Iss: 174 (3), pp. 1555-1563, Nov. 1, 2006.
Iida et al., Catalog of 77 Single-Nucleotide Polymorphisms (SNPs) in the Carbohydrate Sulfotransferase 1 (CHST1) and Carbohydrate Sulfotransferase 3 (CHST3) Genes, *Journal of Human Genetics*, vol. Iss: 47, pp. 14-19, Jan. 1, 2002.
Jonasdottir et al., A Whole Genome Association Study with Icelandic Multiple Sclerosis Patients with 4804 Markers, *Journal of Neuroimmunology*, vol. Iss: 143, pp. 88-92, Jan. 1, 2003.
Ke et al., The Impact of SNP Density on Fine-Scale Patterns of Linkage Disequilibrium, *Human Molecular Genetics*, vol. Iss: 13 (96), pp. 577-588, Jan. 1, 2004.
Kerr et al., An Efficient Algorithm for Segregation Analysis in Large Populations, *J. Anim. Breed. Genet.*, vol. Iss: 113, pp. 457-469, Jan. 1, 1996.
Kinghorn et al., Genetic Evaluation at Individual QTL, *Animal Biotechnology*, vol. Iss: 8, pp. 63-68, Jan. 1, 1997.
Knehr, Michael, Examiner's Report for EP Patent Application No. 30808636.9, *EP Patent Office*, pp. 1-9, Feb. 18, 2010.
Knoblauch et al., Common Haplotypes in Five Genes Influence Genetic Variance of LDL and HDL Cholesterol in the General Population, *Human Molecular Genetics*, vol. Iss: 11 (12), pp. 1477-1485, Jan. 1, 2002.
Kruglyak, Leonid, Prospects for Whole-Genome Linkage Disequilibrium Mapping of Common Disease Genes, *Nature Genetics*, vol. Iss: 22, pp. 139-144, Jun. 1, 1999.
MacKenzie, Jennifer, Spotlight on Gene Markers for Beef, *The Journal* (Newcastle, England), pp. 1-2, Jan. 26, 2006.
Matsuda et al., The Genetic Variance for Multiple Linked Quantitative Trait Loci Conditional on Marker Information in a Crossed Population, *Heredity*, vol. Iss: 88, pp. 2-7, Jan. 1, 2002.
McLean et al., Effects of Milk Protein Genetic Variants on Milk Yield and Composition, *Journal of Dairy Research*, vol. Iss: 51, pp. 531-546, Jan. 1, 1984.
McPeek et al., Assessment of Linkage Disequilibrium by the Decay of Haplotype Sharing with Application to Fine-Scale Genetic Mapping, *Am. J. Hum. Genetics*, vol. Iss: 65, pp. 858-875, Sep. 1, 1999.
Meuwissen et al., Prediction of Total Genetic Value Using Genome-Wide Dense Marker Maps, *Genetics*, vol. Iss: 157, pp. 1819-1829, Apr. 1, 2001.
Meuwissen et al., The Use of Marker Haplotypes in Animal Breeding Schemes, *Genet Sel Evol*, vol. Iss: 28, pp. 161-176, Jan. 1, 1996.
Montaldo et al., Use of Molecular Markers and Major Genes in the Genetic Improvement of Livestock, *Electronic Journal of Biotechnology*, vol. Iss: 1 (2), pp. 83-89, Aug. 15, 1998.
Morton et al., Tests and Estimates of Allelic Association in Complex Inheritance, *Proc. Natl. Acad. Sci. of the USA*, vol. Iss: 95 (19), pp. 11389-11393, Sep. 1, 1998.
Mosig et al., A Whole Genome Scan for Quantitative Trait Loci Affecting Milk Protein Percentage in Israeli-Holstein Cattle, by Means of Selective Milk DNA Pooling in a Daughter Design, Using an Adjusted False Rate Criterion, *Genetics*, vol. Iss: 157, pp. 1683-1698, Apr. 1, 2001.
Notwotny et al., SNP Analysis to Dissect Human Traits, *Current Opinion in Neurobiology*, vol. Iss: 11, pp. 637-641, Jan. 1, 2001.
Peck, Clint, Marker-Assessment Management, *Beef Magazine*, pp. 1-3, May 1, 2001.
Raadsma et al., Predicting Genetic Merit for Mastitis and Fertility in Dairy Cattle Using Genome Wide Selection and High Density SNP Screens, *Animal Genomics for Animal Health Dev. Biol.*, vol. Iss: 132, pp. 219-223, Jan. 1, 2008.
Risch et al., The Future of Genetic Studies of Complex Human Diseases, *Science*, vol. Iss: 273, pp. 1516-1517, Sep. 13, 1996.
Risch, Neil, Linkage Strategies for Genetically Complex Traits. 1. Multilocus Models, *American Journal of Human Genetics*, vol. Iss: 46, pp. 222-228, Feb. 1, 1990.
Romeril, Callum, Examiner's Report for NZ Patent Application No. 541566, *NZ Patent Office*, pp. 1-2, Jun. 3, 2009.
Romeril, Callum, Examiner's Report for NZ Patent Application No. 541566, *NZ Patent Office*, pp. 1-3, Oct. 9, 2009.
Romeril, Callum, Examiner's Report for NZ Patent Application No. 541566, *NZ Patent Office*, vol. Iss: 1-3, Jun. 21, 2010.

Sabeti et al., Detecting Recent Positive Selection in the Human Genome from Haplotype Structure, *Nature*, vol. Iss: 419, pp. 832-837, Oct. 24, 2002.

Schork et al., A Biometric Genome Search in Rats Reveals the Multigenetic Basis of Blood Pressure Variation, *Genome Research*, vol. Iss: 5, pp. 164-172, Jan. 1, 1995.

Schrooten, Whole Genome Scan to Detect Chromosomal Regions Affecting Multiple Traits in Dairy Cattle, *Journal of Dairy Science*, vol. Iss: 87 (10), pp. 3550-3560, Jan. 1, 2004.

Sham et al., DNA Pooling: A Tool for Large-Scale Association Studies, *Nature Rev Genet*, vol. Iss: 3, pp. 862-871, Nov. 1, 2002.

Sisson, Bradley L., International Search Report and Written Opinion for PCT Application No. PCT/US04/35274, *U.S. Searching Authority*, pp. 1-16, Jul. 19, 2007.

Sisson, Bradley L., Office Action Issued for U.S. Appl. No. 10/972,079, *U.S. PTO Office Action*, pp. 1-16, Mar. 23, 2007.

Sisson, Bradley L., Office Action Issued for U.S. Appl. No. 10/972,079, *U.S. PTO Office Action*, pp. 1-14, Jul. 21, 2008.

Sisson, Bradley L., Office Action Issued for U.S. Appl. No. 10/972,079, *U.S. PTO Office Action*, pp. 1-15, Jun. 10, 2009.

Sisson, Bradley L., Office Action Issued for U.S. Appl. No. 12/604,811, *U.S. PTO Office Action*, pp. 1-8, Apr. 30, 2010.

Sisson, Bradley L., Office Action Issued for U.S. Appl. No. 12/604,811, *U.S. PTO Office Action*, pp. 1-9, Sep. 1, 2010.

Soller et al., Restriction Fragment Length Polymorphisms in Poultry Breeding, *Poultry Science*, vol. Iss: 65, pp. 1474-1488, Aug. 1, 1986.

Soller, M., Marker Assisted Selection—An Overview, *Animal Biotechnology*, vol. Iss: 5 (2), pp. 193-207, Jan. 1, 1994.

Sonstegard et al., Dairy Cattle Genomics: Tools to Accelerate Genetic Improvement?, *Journal of Animal Science*, vol. Iss: 79 (E Suppl.), pp. E307-E315, Jan. 1, 2001.

Spelman, R.J., Major Factors in Marker-Assisted Selection Genetic Response in Dairy Cattle Populations, *Proc. 6th World Congress on Genet Applied to Livestock Prod*, vol. Iss: 26, pp. 365-368, Jan. 1, 1998.

Switzer, Juliet Caroline, Office Action Issued for U.S. Appl. No. 10/972,079, *U.S. PTO Office Action*, pp. 1-14, Aug. 18, 2006.

Temple, Examination Report for NZ Patent Application No. 541566, *NZ Patent Office*, pp. 1-2, Feb. 14, 2011.

Thallman et al., Applications of Molecular Selection to DNA Fragments that Contain Microsatellites, *Proc. 5th World Congress on Genet Applied to Livestock Prod*, vol. Iss: 21, pp. 109-112, Jan. 1, 1994.

Thomas, David C., USPTO, Office Action for U.S. Appl. No. 10/750,622, *U.S. PTO Office Action*, pp. 1-12, Apr. 10, 2007.

Thomas, David C., USPTO, Office Action for U.S. Appl. No. 10/750,623, *U.S. PTO Office Action*, pp. 1-18, Oct. 2, 2007.

Thomas, David C., Office Action for U.S. Appl. No. 12/069,845, *U.S. PTO Office Action*, pp. 1-12, May 29, 2009.

Vallet et al., Allelic Variation in the Erythropoietin Receptor Gene is Associated with Uterine Capacity and Litter Size in Swine, *Animal Genetics*, vol. Iss: 36 (2), pp. 97-103, Jan. 1, 2005.

Van Arendonk et al, Use of Multiple Genetic Markers in Prediction of Breeding Values, *Genetics*, vol. Iss: 137, pp. 319-329, May 1, 1994.

Van Arendonk et al., Detection and Exploitation of Markers Linked to Quantitative Traits in Farm Animals, *Proc. 5th World Congress on Genet Applied to Livestock Prod*, vol. Iss: 21, pp. 193-200, Jan. 1, 1994.

Veerkamp et al., Genetics and Genomics to Improve Fertility in High Producing Dairy Cows, *Theriogenology*, vol. Iss: 68S, pp. S266-273, Sep. 1, 2007.

Verrier, Etienne, Marker Assisted Selection for the Improvement of Two Antagonistic Traits Under Mixed Inheritance, *Genet Sel Evol*, vol. Iss: 33, pp. 17-38, Jan. 1, 2001.

Whittaker et al., Marker-Assisted Selection Using Ridge Regression, *Genetic Research*, vol. Iss: 75, pp. 249-252, Jan. 1, 2000.

Zhang et al., Mapping Quantitative Trait Loci for Milk Production and Health of Dairy Cattle in a Large Outbred Population, *Genetics*, vol. Iss: 149, pp. 1959-1973, Aug. 1, 1998.

Antonellis et al., "*Bos tarus* Clone RP42-311M4, Working Draft Sequence", GeneBank Accession No. AC147495, Dec. 2003.

Green, E. D., "NISC Comparative Sequencing Initiative", GeneBank Accession No. GI21724096, Sep. 2002.

Lin et al., "Bovine BAC End Sequences from Library TAMBT", GeneBank Accession No. CC914719, Aug. 2003.

Lucentini, J., "Gene Association Studies Typically Wrong: Reproducible Gene-Disease Associations are Few and Far Between", The Scientist, Dec. 2004, 18: 20.

Wacholder et al., "Assessing the Probability that a Positive Report is False: An Approach for Molecular Epidemiology Studies", Journal of National Cancer Institute, Mar. 2004, 96: 434-442.

"Office Action issued against U.S. Appl. No. 10/750,185", Feb. 2009.

"Office Action issued against U.S. Appl. No. 12/069,845", Mar. 2009.

International Search Report, Mar. 16, 2009.

\* cited by examiner

COMPOSITIONS, METHODS AND SYSTEMS FOR INFERRING BOVINE BREED

CROSS REFERENCE TO RELATED APPLICATION

This application is a continuation of U.S. patent application Ser. No. 10/750,622 filed on Dec. 31, 2003, which claims priority to U.S. provisional patent application 60/437,482 filed on Dec. 31, 2002, both of which are incorporated herein by reference in their entirety.

The specification hereby incorporates by reference in their entirety under 37 C.F.R. §1.77(b)(4), the files contained on the two compact discs filed herewith. The first compact disc includes a file entitled "MMI-0105Table 5.txt", created Aug. 20, 2004, which is 2,818 kbytes in size, and a file entitled "MMI-0105Table 6.txt", created Aug. 20, 2004, which is 25,028 kbytes in size. The first compact disc are duplicates as required under 37 C.F.R. §1.52(e)(4). The third compact disc includes a file entitled "MMI-0105SequenceListing.txt", created Jul. 16, 2004, which is 86,000 kbytes in size.

BACKGROUND OF THE INVENTION

1. Field of the Invention

The invention relates generally to genetic markers and more specifically to polymorphisms associated with bovine breed.

2. Background Information

Classification of individual animals in a livestock population has often relied on a priori groupings of individual animals on the basis of parentage and registration with a Breed Association. If these criteria are not known or not available, animals can be classified as a member of a breed or combination of breeds based on phenotype or geographic location. For example, a bovine animal with a black coat color is frequently classified as an Angus—a breed distinguished by having a black coat color. Further, a bovine animal with a pronounced hump over the shoulder region, pendulous ears and loose skin on dewlap and throat is classified as Brahman. These phenotypes such as coat color, ear and hump appearance are readily observable by livestock producers and frequently used for the basis of breed classification.

Two possible options for classifying an individual bovine animal into a population are:
1) Assign an animal to a population based on known or assumed parentage, phenotypic appearance or trait value for some phenotype, or
2) From a set of predefined populations (such as breeds), sample DNA from a number of members of each population to estimate allele frequencies in each population. Using the allele frequencies, it is possible to compute the likelihood a given genotype originated in each population and individuals can be assigned to population on the basis of these likelihoods (Pritchard, J. K., et al., *Genetics* 155: 945-959 (2000)).

Both strategies (above) rely on defining a set of populations. A classification based on phenotype or geographic locality may not accurately describe the genetic structure of a population if similar phenotypes can arise despite differences in genotype (Rosenberg, N. A., et al., *Genetics*. 159: 699-713 (2001)). Coat color in cattle is determined by one or a few loci that are inherited in a well-known manner (Olson, T. A. 1999. Genetics of colour variation. In: Fries, R. and Ruvinsky, A. (eds.) The Genetics of Cattle—CABI Publishing, Wallingford.). It is relatively easy for livestock breeders to introgress new genes for coat color into a population (such as a breed) resulting in phenotypes that were not previously present.

Some beef marketing systems rely on accurate determination of breed of animal. Of the 41 brands of beef certified by the USDA, 33 name a breed and of these, 30 name Angus, two name Hereford and one names Piedmontese (Smith, G. C., available on the internet at ansci.colostate.edu/ran/beef/smith7.pdf). To date, the only methods available to qualify animals for these systems are known or assumed parentage or phenotypic appearance. There is an opportunity to improve accuracy of individual animal qualification using the allele frequencies to compute the likelihood that a given genotype originated in specific breed population.

It is critical to know the breed of cattle entered into and qualifying from branded beef programs when those branded beef programs include breed specifications. In particular, knowledge of breed composition is important for the following:
1) to verify claims for breed type or breed composition associated with breed-specific marketing programs. Verification of claims for breed type or breed composition has not been possible because no available technology could classify a bovine animal to a particular population or infer the breed composition of an individual animal. Currently, the only bovines accepted by breed are those within the seedstock sector where the records of individual animals are maintained by Breed Associations or in commercial populations where cattle are recorded in a performance registry—usually by a Breed Association. These total breed-identified cattle likely comprise some five percent of the national beef cattle population. Therefore, standardization of claims for breed or breed type is very loose and limited to a small fraction of animals contributing to the beef supply; and
2) to implement management strategies for the feeding of cattle to optimize the pre-harvest growth and development and post-harvest fabrication of their associated beef products. Efficiencies in production from feeding, sorting, managing and marketing cattle can be obtained by identifying and matching breed-specific phenotypic data for feedlot, carcass and meat quality traits. Where breeds cannot be distinguished on the merit of parentage and simply measured phenotypic differences, a purely genetic analysis provides the most suitable test to assign animals to a population (Rosenberg, N. A., et al., *Genetics* 159: 699-713 (2001)). Only if a correspondence between genotype and known parentage classification is established can these characteristics also serve as appropriate classification tools.

Accordingly, there remains a need for methods and compositions that provide information regarding bovine breed.

SUMMARY OF THE INVENTION

The present invention is based, in part, on the discovery of bovine single nucleotide polymorphism (SNP) markers that are associated with, and predictive of, bovine breeds including, but not limited to, Angus, Brahman, Charolais, Hereford, Simmental, Gelbvieh, Limousin, and Beefmaster breeds. Accordingly, the present invention provides methods to discover and use single nucleotide polymorphisms (SNP) for identifying breed, or line and breed, or line composition of a bovine subject. The present invention further provides specific nucleic acid sequences, SNPs, and SNP patterns that can be used for identifying breed or breed combinations for Angus, Limousin, Brahman, Hereford, Simmental, Gelbvieh, Charolais and Beefmaster breeds. These patterns can be utilized to manage animals in a feedlot to obtain optimum performance based on known characteristics of specific breeds. In another embodiment, cattle can be marketed prior to harvest based on their breed characteristics for meat production. In another aspect, branded products based on breed designation can certify their label based on specific breed markers.

Accordingly, in one embodiment the present invention provides a method to infer breed of a bovine subject from a nucleic acid sample of the bovine subject, that includes identifying in the nucleic acid sample, at least one nucleotide occurrence of at least one single nucleotide polymorphism (SNP) corresponding to position 300 of any one of SEQ ID NOS:1 to 4868 or SEQ ID NOS:64887 to 64895, wherein the SNP is associated with a breed, thereby inferring the breed of the bovine subject. A SNP is associated with a breed when at least one nucleotide occurrence of the SNP occurs more frequently in subjects of a particular breed than other breeds in a statistically significant manner, for example with greater than 80%, 85%, 90%, 95%, or 99% confidence. Therefore, in certain aspects, the methods include identifying whether the nucleotide occurrence is a bovine SNP allele identified herein as associated with bovine breed. In certain aspects, the identified breed includes, but is not limited to, Angus, Limousin, Brahman, Simmental, Hereford, Gelbvieh or Charolais. Furthermore, in certain aspects, at least one nucleotide occurrence of at least one SNP listed in Table 5 or Table 3A as associated with Angus cattle is identified.

In another embodiment, the present invention provides a method for determining a nucleotide occurrence of a single nucleotide polymorphism (SNP) in a bovine sample, that includes contacting a bovine polynucleotide in the sample with an oligonucleotide that binds to a target region of any one of SEQ ID NOS:1 to 4868 or SEQ ID NOS:64887 to 64895, and determining the nucleotide occurrence of a single nucleotide polymorphism (SNP) corresponding to position 300 of any one of SEQ ID NOS:1 to 4868 or SEQ ID NOS:64887 to 64895. The determination typically includes analyzing binding of the oligonucleotide, or detecting an amplification product generated using the oligonucleotide, thereby determining the nucleotide occurrence of the SNP.

In another embodiment, the present invention provides an isolated polynucleotide that includes a fragment of at least 20 contiguous nucleotides, a polynucleotide at least 90% identical to the fragment of 20 contiguous nucleotides, or a complement thereof, wherein the isolated polynucleotide includes a nucleotide occurrence of a single nucleotide polymorphism (SNP) associated with breed, wherein the SNP corresponds to position 300 of any one of SEQ ID NOS:1 to 4868 or SEQ ID NOS:64887 to 64895.

In yet another embodiment, the present invention provides an isolated oligonucleotide that includes 10 nucleotides, that selectively binds to a target polynucleotide of SEQ ID NOS:1 to 4868 or SEQ ID NOS:64887 to 64895, wherein a terminal nucleotide of the isolated oligonucleotide binds to position 299, 300, or 301 of any one of SEQ ID NOS:1 to 4868 or SEQ ID NOS:64887 to 64895.

DETAILED DESCRIPTION OF THE INVENTION

The specification hereby incorporates by reference in their entirety, the files contained on the two compact discs filed herewith. Two copies of each of the two compact discs are filed herewith. The first compact disc includes a file called "MMI1150 Table 5.doc," created Dec. 31, 2003, which is 4770 kilobytes in size, and a file called "MMI1150 Table 6.doc," created Dec. 31, 2003, which is 8575 kilobytes in size. The Second disc includes a sequence listing which is included in a file called "MMI1150 SEQUENCE LISTING.txt," created Dec. 31, 2003, which is 88096 kilobytes in size.

LENGTHY TABLES

The patent contains a lengthy table section. A copy of the table is available in electronic form from the USPTO web site (http://seqdata.uspto.gov/?pageRequest=docDetail&DocID=US08026064B2). An electronic copy of the table will also be available from the USPTO upon request and payment of the fee set forth in 37 CFR 1.19(b)(3).

The present invention is based in part on the discovery of single nucleotide polymorphisms (SNPs) that can be used to infer breed of a bovine subject. Accordingly, provided herein is a method for inferring the breed of a bovine subject from a nucleic acid sample of the bovine subject, by identifying in the sample, a nucleotide occurrence for at least one single nucleotide polymorphism (SNP), wherein the nucleotide occurrence is associated with the breed. In certain aspects, the SNP corresponds to position 300 of any one of SEQ ID NOS:1 to 4868 or SEQ ID NOS:64887 to 64895.

Using the teachings herein, SNPs associated with any breed of cattle can be identified. Therefore, methods of the present invention for inferring breed of a bovine subject, can be used to infer the breed of any bovine subject. For example, the methods can be used to infer a breed including, but not limited to, Angus, Limousin, Brahman, Simmental, Hereford, Holstein, Gelbvieh or Charolais cattle. In certain aspects, the methods are used to infer an Angus from a non-Angus breed. Furthermore, the methods of the present invention can be used to assign a breed or breeds to an individual animal with a specific probability. Typically, an identified nucleotide occurrence is compared to multiple known SNP alleles associated with multiple breeds, for example the breed associated alleles identified herein in Tables 5 and 3A, to infer a breed for a subject from multiple possible breeds.

The Example provided herein illustrates the use of whole genome shotgun sequencing and genotyping analysis to identify SNPs that can be used to infer breed of a bovine subject. For this analysis, genomic DNA libraries were constructed from six breeds of cattle (Angus, Limousin, Brahman, Simmental, Holstein and Charolais). The libraries were a mixture of 2.5, and 10 kilobase inserts. Libraries from four of the cattle breeds (Angus, Brahman, Simmental and Limousin) were sequenced, using the whole genome shotgun sequencing method developed by Celera Genomics (Venter, J. C. et al. (2001) *Science* 291:1304), to a depth of coverage sufficient to generate putative SNPs. The distribution of sequence fragments obtained from the cattle breeds was 32% Angus, 35% Limousin, 33% Brahman, and less than 1% Simmental.

Allele frequencies within breed were determined using simple counting methods. Four thousand eight hundred and seventy seven breed specific markers (See SEQ ID NOS:1 to 4868 (Tables 5 and 6, included on a compact disc filed herewith) and SEQ ID NOS:64887 to 64895 (Tables 3A and 3B)) were identified by analysis of over 19,000 markers tested.

Details of the SNP markers that were identified as informative for breed, are listed in Tables 5 and 6 (filed herewith on a compact disc) and Tables 3A and 3B. Tables 3A and 5 provide the names of the identified SNP markers, breed specific alleles, their associated breed, allele frequencies, and breeds for which the alleles, and therefore SNPs, are most significantly associated (referred to as "major breeds" in the table). A SNP was identified as being associated with a breed when the frequency of at least one allele was significantly greater for at least one breed than for other breeds. Tables 3B and 6 provide primer sequences (See "Forward," "Reverse," and "Extension") that were used to amplify a region that includes the SNP, and amplicon sequences that indicate the nucleotide occurrences for the SNP that were identified in brackets within the sequence.

Accordingly, in one aspect, the method identifies at least one nucleotide occurrence of at least one SNP listed in Table 5 or Table 3A as associated with Angus cattle. In another aspect, the method identifies at least one nucleotide occurrence of at least one SNP listed in Table 5 or Table 3A as associated with Brahman cattle. In another aspect, the method identifies at least one nucleotide occurrence of at least one SNP listed in Table 5 or Table 3A as associated with Limousin cattle. In yet another aspect, the method identifies at least one nucleotide occurrence of at least one SNP listed in Table 5 or Table 3A as associated with Simmental cattle. In still another aspect, the method identifies at least one nucleotide occurrence of at least one SNP listed in Table 5 or Table 3A as associated with Hereford cattle. In another aspect, the method identifies at least one nucleotide occurrence of at least one SNP listed in Table 5 or Table 3A as associated with Charolais cattle. In another aspect, the method identifies at least one nucleotide occurrence of at least one SNP listed in Table 5 or Table 3A as associated with Gelbvieh cattle.

In certain aspects, the method further includes marketing the bovine subject prior to harvest based on the inferred breed. As indicated herein, some beef marketing systems rely on accurate determination of a breed of an animal. For example, in certain aspects the inferred breed is used to assign beef of a bovine subject to a USDA certified brand before the subject is harvested.

In another aspect, the method further includes managing the bovine subject in the feedlot to obtain improved performance based on known characteristics of the inferred breed for the subject. In fact, the SNPs and methods of the present invention can be used to identify the percentage of each breed comprising an individual animal. In this aspect, for example, animals arriving to the feedlot can have a DNA sample taken at processing. The sample can be screened against breed specific DNA markers to determine the percentage of breed per animal based on the breed specific marker panel and the degree of accuracy required. These data can be used to manage feedlot cattle for specific growth and development traits. In one aspect, cattle identified from the exotic breed type (Charolais, Gelbvieh, Limousin, and Simmental) have high growth rate and large harvest sizes. These cattle can be managed to maximize growth rate and lean meat yield. Cattle identified as English type (Angus and Hereford) produce high quality meat products and can be marketed into the high quality yield grade.

In other examples, methods of the present invention further include identifying a nucleotide sequence of a hypermutable sequence in the sample, and inferring breed based on at least one SNP nucleotide occurrence and the nucleotide sequence of the hypermutable sequence. Hypermutable sequences include, for example, microsatellite nucleic acid sequences In another aspect, a method of the present invention further includes branding or marketing a product of the bovine subject based on the inferred breed, including marketing the product under a trademark specific for breed. Breed specified products can certify that the product is in fact from the breed labeled, thereby increasing consumer confidence in a product and increasing the value of a product.

The method can include a determination of the nucleotide occurrence of at least 2 SNPs. At least 2 SNPs can form all or a portion of a haplotype, wherein the method identifies a haplotype allele that is associated with a specific breed. Furthermore, the method can include identifying a diploid pair of haplotype alleles.

In another embodiment, the present invention provides a method for sorting one or more bovine subjects, that includes inferring a breed for a first bovine subject from a nucleic acid sample of the first bovine subject, by identifying a nucleotide occurrence of at least one single nucleotide polymorphism (SNP) corresponding to position 300 of at least one of SEQ ID NOS:1 to 4868 or SEQ ID NOS:64887 to 64895, wherein the SNP is associated with breed. The first bovine subject is sorted based on the inferred breed. The method can then be repeated for additional subjects, thereby sorting bovine subjects. The bovine subjects can be sorted, for example, based on whether they are Angus, Limousin, Brahman, Simmental, Hereford, Gelbvieh or Charolais cattle.

In another embodiment, the present invention provides a method of providing labeling accuracy for breed identified meat products, that includes inferring breed of a bovine candidate for use in branded meat products from a nucleic acid sample of the bovine candidate by a method comprising identifying the nucleotide occurrence of at least one single nucleotide polymorphism (SNP) corresponding to position 300 of at least one of SEQ ID NOS:1 to 4868 or SEQ ID NOS:64887 to 64895, wherein the SNP is associated with breed; and determining whether to brand the harvested product based on the inferred breed. This method provides quality assurance guarantees of the label brand. In certain aspects, for example, the inferred breed is Angus, Limousin, Brahman, Simmental, Hereford, Gelbvieh or Charolais.

In yet another embodiment, the present invention provides a method for breeding a bovine subject, that includes inferring breed of a bovine candidate for use in breeding programs from a nucleic acid sample of the bovine candidate by a method that includes identifying the nucleotide occurrence of at least one single nucleotide polymorphism (SNP) corresponding to position 300 of at least one of SEQ ID NOS:1 to 4868 or SEQ ID NOS:64887 to 64895, wherein the SNP is associated with breed. A determination is made on whether to select the individual for use in breeding programs based on the inferred breed, thereby breeding the bovine subject.

The selection is implemented, in certain aspects, at the elite or breeding nucleus level or at the multiplier or foundation animal level. In another embodiment, the present invention provides a bovine subject resulting from the selection and breeding.

In another embodiment, the present invention provides a method for identifying a bovine single nucleotide polymorphism (SNP) informative of breed, that includes performing whole genome shotgun sequencing of a bovine genome, and genotyping at least two bovine subjects from at least two breeds, thereby identifying the bovine single nucleotide polymorphisms informative of breed. The Example provided herein, illustrates the use of this method to identify breed SNPs.

As used herein, the term "at least one", when used in reference to a gene, SNP, haplotype, or the like, means 1, 2, 3, 4, 5, 6, 7, 8, 9, 10, etc., up to and including all of the haplotype alleles, genes, haplotypes, and/or SNPs of the bovine genome. Reference to "at least a second" gene, SNP, haplotype or the like, means two or more, i.e., 2, 3, 4, 5, 6, 7, 8, 9, 10, etc., bovine genes, SNPs, haplotypes, or the like.

Polymorphisms are allelic variants that occur in a population that can be a single nucleotide difference present at a locus, or can be an insertion or deletion of one, a few or many consecutive nucleotides. As such, a single nucleotide polymorphism (SNP) is characterized by the presence in a population of one or two, three or four nucleotides (i.e., adenosine, cytosine, guanosine or thymidine), typically less than all four nucleotides, at a particular locus in a genome such as the human genome. It will be recognized that, while the methods of the invention are exemplified primarily by the detection of SNPs, the disclosed methods or others known in the art similarly can be used to identify other types of bovine polymorphisms, which typically involve more than one nucleotide. A SNP is associated with a breed when at least one nucleotide occurrence of the SNP occurs more frequently in subjects of a particular breed in a statistically significant manner, for example with greater than 80%, 85%, 90%, 95%, or 99% confidence. A bovine "SNP allele" is a nucleotide occurrence of a SNP within a population of bovine animals.

In another embodiment, the present invention provides an isolated polynucleotide that includes a fragment of at least 20 contiguous nucleotides of any one of SEQ ID NOS:1 to 4868 or SEQ ID NOS:64887 to 64895, a polynucleotide at least 90% identical to the 20 contiguous nucleotide fragment, or a complement thereof, wherein the isolated polynucleotide includes a nucleotide occurrence of a single nucleotide polymorphism (SNP) that corresponds to position 300 of SEQ ID NOS:1 to 4868 or SEQ ID NOS:64887 to 64895.

In certain aspects, the isolated polynucleotide, for example, includes a fragment of at least 5, 10, 15, 20, 25, 30, 35, 40, 45, 50, 100, 200, 250, 500, or 600 contiguous nucleotides of any one of SEQ ID NOS:1 to 4868 or SEQ ID NOS:64887 to 64895. In another aspect, the isolated polynucleotide is at least 65, 70, 75, 80, 85, 90, 95, 96, 97, 98, 99, or 99.5% identical to SEQ ID NOS:1 to 4868 or SEQ ID NOS:64887 to 64895, for example. Typically, the isolated nucleotide includes a region that is contiguous with a region of any one of SEQ ID NOS:1 to 4868 or SEQ ID NOS:64887 to 64895 that includes position 300. In certain aspects, the isolated polynucleotide consists of any one of SEQ ID NOS:1 to 4868 or SEQ ID NOS:64887 to 64895 in its entirety. In other aspects, the isolated polynucleotide consists of any one of SEQ ID NOS:4869 to 19472 or SEQ ID NOS:64896 to 64922.

The polynucleotide or an oligonucleotide of the invention can further include a detectable label. For example, the detectable label can be associated with the polynucleotide at a position corresponding to position 300 of any one of SEQ ID NOS:1 to 4868 or SEQ ID NOS:64887 to 64895. As discussed in more detail herein, the labeled polynucleotide can be generated, for example, during a microsequencing reaction, such as SNP-IT™ reaction.

Detectable labeling of a polynucleotide or oligonucleotide is well known in the art. Particular non-limiting examples of detectable labels include chemiluminescent labels, fluorescent labels, radiolabels, enzymes, haptens, or even unique oligonucleotide sequences.

In another embodiment, the present invention provides an isolated vector that includes a polynucleotide disclosed hereinabove. The term "vector" refers to a plasmid, virus or other vehicle known in the art that has been manipulated by insertion or incorporation of a nucleic acid sequence.

Methods that are well known in the art can be used to construct vectors, including in vitro recombinant DNA techniques, synthetic techniques, and in vivo recombination/genetic techniques (See, for example, the techniques described in Maniatis et al. 1989 Molecular Cloning A Laboratory Manual, Cold Spring Harbor Laboratory, N.Y., incorporated herein in its entirety by reference).

In another aspect, the present invention provides an isolated cell that includes the vector. The cell can be prokaryotic or eukaryotic. Techniques for incorporated vectors into prokaryotic and eukaryotic cells are well known in the art. In certain aspects, the cells are bovine cells. In other aspects, the cells are bacterial cells. In still other aspects, the cells are human cells.

In another aspect, the present invention provides a primer pair that binds to a first target region and a second target region of SEQ ID NOS:1 to 4868 or SEQ ID NOS:64887 to 64895, wherein the first primer of the primer pair and a second primer of the primer pair are at least 10 nucleotides in length and bind opposite strands of the target region located within 3000 nucleotides of a position corresponding to position 300 of any one of SEQ ID NOS:1 to 4868 or SEQ ID NOS:64887 to 64895, and prime polynucleotide synthesis from the target region in opposite directions across position 300. In another embodiment, provided herein is a primer pair that binds to a first target region and a second target region of SEQ ID NOS:1 to 4868 or SEQ ID NOS:64887 to 64895, wherein a first primer of the primer pair and a second primer of the primer pair are at least 10 nucleotides in length, bind opposite strands of the target region, and prime polynucleotide synthesis from the target region in opposite directions across position 300 of SEQ ID NOS:1 to 4868 or SEQ ID NOS:64887 to 64895.

In another embodiment, the present invention provides an isolated oligonucleotide that selectively binds to a target polynucleotide that includes at least 5, 10, 15, 20, 25, 30, 35, 40, 45, 50, 100, 150, 300, 500, or 600 nucleotides SEQ ID NOS:1 to 4868 or SEQ ID NOS:64887 to 64895, or a complement thereof, wherein the terminal nucleotide corresponds to position 299, 300, or 301. In another embodiment, the present invention provides an isolated oligonucleotide that includes 10 nucleotides, which selectively binds to a target polynucleotide of any one of SEQ ID NOS:1 to 4868 or SEQ ID NOS:64887 to 64895, wherein a terminal nucleotide of the isolated oligonucleotide binds to position 298, 299, 300, 301, or 302 of any one of SEQ ID NOS:1 to 4868 or SEQ ID NOS:64887 to 64895. The oligonucleotide can be, for example, 10, 15, 20, 25, 50, or 100 nucleotides in length. In certain aspects, the terminal nucleotide binds to position 300 of any one of SEQ ID NOS:1 to 4868 or SEQ ID NOS:64887 to 64895.

In another embodiment, the present invention provides an isolated oligonucleotide pair effective for determining a nucleotide occurrence at a single nucleotide polymorphism (SNP) corresponding to position 300 of any one of SEQ ID NOS:1 to 4868 or SEQ ID NOS:64887 to 64895, wherein each isolated oligonucleotide comprises at least 5 nucleotides from SEQ ID NOS:1 to 4868 or SEQ ID NOS:64887 to 64895 and wherein the terminal nucleotide of each oligonucleotide pair is complementary to a different nucleotide at position 300 of any one of SEQ ID NOS:1 to 4868 or SEQ ID NOS:64887 to 64895 or a complement thereof. In certain aspects, the specific binding pair member is a substrate for a primer extension reaction.

As used herein, "about" means within ten percent of a value. For example, "about 100" would mean a value between 90 and 110.

The term "haplotypes" as used herein refers to groupings of two or more SNPs that are physically present on the same chromosome which tend to be inherited together except when recombination occurs. The haplotype provides information regarding an allele of the gene, regulatory regions or other genetic sequences affecting a trait. The linkage disequilibrium and, thus, association of a SNP or a haplotype allele(s) and a bovine breed can be strong enough to be detected using simple genetic approaches, or can require more sophisticated statistical approaches to be identified.

Numerous methods for identifying haplotype alleles in nucleic acid samples are known in the art. In general, nucleic acid occurrences for the individual SNPs are determined and then combined to identify haplotype alleles. There are several algorithms for haplotype reconstruction based on pedigree analysis. These are the Maximum Likelihood methods ((Excofier, L., and Slatkin, M., *Mol. Biol. Evol.* 12: 921-927 (1995)), the parsimony method created by Clark, A. G., *Mol. Biol. Evol.* 7: 111-122 (1990) and the phase reconstruction method of Stephens, M., et al., *Am. J. Hum. Genet.* 68:978-989, 2001, which is incorporated herein by reference). These methods can be applied to the data generated, regarding individual nucleotide occurrences in SNP markers of the subject, in order to determine alleles for each haplotype in a subject's genotype. Alternatively, haplotypes can also be determined directly, for each pair of sites, by allele-specific PCR (Clark, A. G. et al., *Am. J. Hum. Genet.* 63: 595-612 (1998).

As used herein, the term "infer" or "inferring", when used in reference to a breed, means drawing a conclusion about a breed using a process of analyzing individually or in combination, nucleotide occurrence(s) of one or more SNP(s), which can be part of one or more haplotypes, in a nucleic acid sample of the subject, and comparing the individual or combination of nucleotide occurrence(s) of the SNP(s) to known relationships of nucleotide occurrence(s) of the SNP(s) and the breed. As disclosed herein, the nucleotide occurrence(s) can be identified directly by examining nucleic acid molecules, or indirectly by examining a polypeptide encoded by a particular gene where the polymorphism is associated with an amino acid change in the encoded polypeptide.

Relationships between nucleotide occurrences of one or more SNPs or haplotypes and a breed can be identified using known statistical methods. A statistical analysis result which shows an association of one or more SNPs or haplotypes with a breed with at least 80%, 85%, 90%, 95%, or 99% confidence, or alternatively a probability of insignificance less than 0.05, can be used to identify SNPs and haplotypes. These statistical tools may test for significance related to a null hypothesis that an on-test SNP allele or haplotype allele is not significantly different between groups with different traits. If the significance of this difference is low, it suggests the allele is not related to a breed.

In diploid organisms such as bovines, somatic cells, which are diploid, include two alleles for each single-locus haplotype. As such, in some cases, the two alleles of a haplotype are referred to herein as a genotype or as a diploid pair, and the analysis of somatic cells, typically identifies the alleles for each copy of the haplotype. Methods of the present invention can include identifying a diploid pair of haplotype alleles. These alleles can be identical (homozygous) or can be different (heterozygous). Haplotypes that extend over multiple loci on the same chromosome include up to 2 to the Nth power alleles where N is the number of loci. It is beneficial to express polymorphisms in terms of multi-locus (i.e. multi SNP) haplotypes because haplotypes offer enhanced statistical power for genetic association studies. Multi-locus haplotypes can be precisely determined from diploid pairs when the diploid pairs include 0 or 1 heterozygous pairs, and N or N−1 homozygous pairs. When multi-locus haplotypes cannot be precisely determined, they can sometimes be inferred by statistical methods. Methods of the invention can include identifying multi-locus haplotypes, either precisely determined, or inferred.

A sample useful for practicing a method of the invention can be any biological sample of a subject, typically a bovine subject, that contains nucleic acid molecules, including portions of the gene sequences to be examined, or corresponding encoded polypeptides, depending on the particular method. As such, the sample can be a cell, tissue or organ sample, or can be a sample of a biological material such as blood, milk, semen, saliva, hair, tissue, and the like. A nucleic acid sample useful for practicing a method of the invention can be deoxyribonucleic (DNA) acid or ribonucleic acids (RNA). The nucleic acid sample generally is a deoxyribonucleic acid sample, particularly genomic DNA or an amplification product thereof. However, where heteronuclear ribonucleic acid, which includes unspliced mRNA precursor RNA molecules and non-coding regulatory molecules such as RNA, is available, a cDNA or amplification product thereof can be used.

Where each of the SNPs of the haplotype is present in a coding region of a gene(s), the nucleic acid sample can be DNA or RNA, or products derived therefrom, for example, amplification products. Furthermore, while the methods of the invention generally are exemplified with respect to a nucleic acid sample, it will be recognized that particular haplotype alleles can be in coding regions of a gene and can result in polypeptides containing different amino acids at the positions corresponding to the SNPs due to non-degenerate codon changes. As such, in another aspect, the methods of the invention can be practiced using a sample containing polypeptides of the subject.

In one embodiment, DNA samples are collected and stored in a retrievable barcode system, either automated or manual, that ties to a database. Collection practices include systems for collecting tissue, hair, mouth cells or blood samples from individual animals at the same time that ear tags, electronic identification or other devices are attached or implanted into the animal. All identities of animals can be automatically uploaded into a primary database. Tissue collection devices can be integrated into the tool used for placing the ear tag. Body fluid samples can be collected and stored on a membrane bound system.

The sample is then analyzed on the premises or sent to a laboratory where a medium to high-throughput genotyping system is used to analyze the sample.

The subject of the present invention can be any bovine subject, for example a bull, a cow, a calf, a steer, or a heifer or any bovine embryo or tissue.

In another aspect, the present invention provides a system for determining the nucleotide occurrences in a population of bovine single nucleotide polymorphisms (SNPs). The system typically includes a hybridization medium and/or substrate that includes at least two oligonucleotides of the present invention, or oligonucleotides used in the methods of the present invention. The hybridization medium and/or substrate are used to determine the nucleotide occurrence of bovine SNPs that are associated with breed. Accordingly, the oligonucleotides are used to determine the nucleotide occurrence of bovine SNPs that are associated with a breed. The determination can be made by selecting oligonucleotides that bind at or near a genomic location of each SNP of the series of bovine SNPs. The system of the present invention typically includes a reagent handling mechanism that can be used to apply a reagent, typically a liquid, to the solid support. The binding of an oligonucleotide of the series of oligonucleotides to a polynucleotide isolated from a genome can be affected by the nucleotide occurrence of the SNP. The system can include a mechanism effective for moving a solid support and a detection mechanism. The detection method detects binding or tagging of the oligonucleotides.

Accordingly, in another embodiment, the present invention provides a method for determining a nucleotide occurrence of a single nucleotide polymorphism (SNP) in a bovine sample, that includes contacting a bovine polynucleotide in the sample with an oligonucleotide that binds to a target region of any one of SEQ ID NOS:1 to 4868 or SEQ ID NOS:64887 to 64895. The nucleotide occurrence of a single nucleotide polymorphism (SNP) corresponding to position 300 of any one of SEQ ID NOS:1 to 4868 or SEQ ID NOS:64887 to 64895, is then determined, wherein the determination comprises analyzing binding of the oligonucleotide, or detecting an amplification product generated using the oligonucleotide, thereby determining the nucleotide occurrence of the SNP. In certain aspects, the oligonucleotide binds to a target sequence that includes one of the SNPs, and the nucleotide occurrence is determined based on the binding of the oligonucleotide to the target sequence.

In another aspect, the bovine polynucleotide is contacted with a pair of oligonucleotides that constitute a primer pair, and the nucleotide occurrence is determined using an amplification product generated using the primer pair. For example, at least one primer of the primer pair can be one of SEQ ID NOS:Forward1 to Reverse4868. Furthermore, the primer pair, in certain aspects, is any of the forward and reverse primer pairs listed in Table 6 (Appendix 2).

In certain aspects, the terminal nucleotide of the oligonucleotide binds to the SNP. In these aspects, the method can include detecting an extension product generated using the oligonucleotide as a primer. The oligonucleotide, in certain aspects, is any one of SEQ ID NO:4879 to 9736 or SEQ ID NO:64914 to 64922.

In other aspects, the terminal nucleotide of each oligonucleotide of a pair of oligonucleotides is complementary to a different nucleotide at position 300 of any one of SEQ ID NOS:1 to 4868 or SEQ ID NOS:64887 to 64895, or a complement thereof. In another example, the polynucleotide can be contacted with a pair of oligonucleotides each comprising a different detectable label.

Medium to high-throughput systems for analyzing SNPs, known in the art such as the SNPStream® UHT Genotyping System (Beckman/Coulter, Fullerton, Calif.) (Boyce-Jacino and Goelet patents), the Mass Array™ system (Sequenom, San Diego, Calif.) (Storm, N. et al. (2002) *Methods in Molecular Biology*. 212: 241-262.), the BeadArray™ SNP genotyping system available from Illumina (San Diego, Calif.)(Oliphant, A., et al. (June 2002) (supplement to *Biotechniques*), and TaqMan™ (Applied Biosystems, Foster City, Calif.) can be used with the present invention. However, the present invention provides a medium to high-throughput system that is designed to detect nucleotide occurrences of bovine SNPs, or a series of bovine SNPs that can make up a series of haplotypes. Therefore, as indicated above the system includes a solid support or other method to which a series of oligonucleotides can be associated that are used to determine a nucleotide occurrence of a SNP for a series of bovine SNPs that are associated with a trait. The system can further include a detection mechanism for detecting binding of the series of oligonucleotides to the series of SNPs. Such detection mechanisms are known in the art.

The system can be a microfluidic device. Numerous microfluidic devices are known that include solid supports with microchannels (See e.g., U.S. Pat. Nos. 5,304,487, 5,110745, 5,681,484, and 5,593,838).

The SNP detection systems of the present invention are designed to determine nucleotide occurrences of one SNP or a series of SNPs. The systems can determine nucleotide occurrences of an entire genome-wide high-density SNP map.

Numerous methods are known in the art for determining the nucleotide occurrence for a particular SNP in a sample. Such methods can utilize one or more oligonucleotide probes or primers, including, for example, an amplification primer pair that selectively hybridizes to a target polynucleotide, which corresponds to one or more bovine SNP positions. Oligonucleotide probes useful in practicing a method of the invention can include, for example, an oligonucleotide that is complementary to and spans a portion of the target polynucleotide, including the position of the SNP, wherein the presence of a specific nucleotide at the position (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe. These oligonucleotides and probes are another embodiment of the present invention.

An oligonucleotide ligation assay (Grossman, P. D. et al. (1994) *Nucleic Acids Research* 22:4527-4534) also can be used to identify a nucleotide occurrence at a polymorphic position, wherein a pair of probes that selectively hybridize upstream and adjacent to and downstream and adjacent to the site of the SNP, and wherein one of the probes includes a terminal nucleotide complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the SNP site. An example of this type of assay is the SNPlex System (Applied Biosystems, Foster City, Calif.).

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP site can be useful, wherein the amplification product is examined to determine the nucleotide occurrence at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP locus can be sequenced using traditional sequence methodologies (e.g., the "dideoxy-mediated chain termination method," also known as the "Sanger Method" (Sanger, F., et al., J. Molec. Biol. 94:441 (1975); Prober et al. Science 238:336-340 (1987)) and the "chemical degradation method," "also known as the "Maxam-Gilbert method" (Maxam, A. M., et al., Proc. Natl. Acad. Sci. (U.S.A.) 74:5660 (1977)), both references herein incorporated by reference) to determine the nucleotide occurrence at the SNP locus.

Methods of the invention can identify nucleotide occurrences at SNPs using genome-wide sequencing or "microsequencing" methods. Whole-genome sequencing of individuals identifies all SNP genotypes in a single analysis. Microsequencing methods determine the identity of only a single nucleotide at a "predetermined" site. Such methods have particular utility in determining the presence and identity of polymorphisms in a target polynucleotide. Such microsequencing methods, as well as other methods for determining the nucleotide occurrence at a SNP locus are discussed in Boyce-Jacino, et al., U.S. Pat. No. 6,294,336, incorporated herein by reference, and summarized herein.

Microsequencing methods include the Genetic Bit™ Analysis method disclosed by Goelet, P. et al. (WO 92/15712, herein incorporated by reference). Additional, primer-guided, nucleotide incorporation procedures for assaying polymorphic sites in DNA have also been described (Kornher, J. S. et al, Nucleic Acids Res. 17:7779-7784 (1989); Sokolov, B. P., Nucleic Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al, Hum. Mutat. 1:159-164 (1992); Ugozzoli, L. et al., GATA 9:107-112 (1992); Nyren, P. et al., Anal. Biochem. 208:171-175 (1993); and Wallace, WO89/10414). These methods differ from Genetic Bit™ Analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. *Amer. J. Hum. Genet.* (1993) 52:46-59 Other formats for microsequencing include Pyrosequencing (Pyrosequencing AB, Uppsala, Sweden, Alderborn et al (2000) Genome Res. 10:1249-1258).

Alternative microsequencing methods have been provided by Mundy, C. R. (U.S. Pat. No. 4,656,127) and Cohen, D. et al (French Patent 2,650,840; PCT Appln. No. WO91/02087), which discuss a solution-based method for determining the identity of the nucleotide of a polymorphic site. As in the Mundy method of U.S. Pat. No. 4,656,127, a primer is employed that is complementary to allelic sequences immediately 3'- to a polymorphic site.

In response to the difficulties encountered in employing gel electrophoresis to analyze sequences, alternative methods for microsequencing have been developed. Macevicz (U.S. Pat. No. 5,002,867), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a set of probes has been tested.

Boyce-Jacino, et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target.

The occurrence of a SNP can be determined using denaturing HPLC such as described in Nairz K et al (2002) *Proc. Natl. Acad. Sci.* (U.S.A.) 99:10575-80, and the Transgenomic WAVE® System (Transgenomic, Inc. Omaha, Nebr.).

Oliphant et al. report a method that utilizes BeadArray™ Technology that can be used in the methods of the present invention to determine the nucleotide occurrence of a SNP (supplement to Biotechniques, June 2002). Additionally, nucleotide occurrences for SNPs can be determined using a DNAMassARRAY system (SEQUENOM, San Diego, Calif.). This system combines proprietary SpectroChips™, microfluidics, nanodispensing, biochemistry, and MALDI-TOF MS (matrix-assisted laser desorption ionization time of flight mass spectrometry).

As another example, the nucleotide occurrences of bovine SNPs in a sample can be determined using the SNP-IT™ method (Beckman Coulter, Fullerton, Calif.). In general, SNP-IT™ is a 3-step primer extension reaction. In the first step a target polynucleotide is isolated from a sample by hybridization to a capture primer, which provides a first level of specificity. In a second step the capture primer is extended from a terminating nucleotide triphosphate at the target SNP site, which provides a second level of specificity. In a third step, the extended nucleotide trisphosphate can be detected using a variety of known formats, including: direct fluorescence, indirect fluorescence, an indirect calorimetric assay, mass spectrometry, fluorescence polarization, etc. Reactions can be processed in 384 well format in an automated format using a SNPstream™ instrument (Beckman Coulter, Fullerton, Calif.). Reactions can also be analyzed by binding to Luminex biospheres (Luminex Corporation, Austin, Tex., Cai. H. (2000) *Genomics* 66(2):135-43.). Other formats for SNP detection include TaqMan™ (Applied Biosystems, Foster City, Calif.), Rolling circle (Hatch et al (1999) *Genet. Anal.* 15: 35-40, Qi et al (2001) *Nucleic Acids Research* Vol. 29 e 116), fluorescence polarization (Chen, X., et al. (1999) Genome Research 9:492-498), SNaPShot (Applied Biosystems, Foster City, Calif.) (Makridakis, N. M. et al. (2001) *Biotechniques* 31:1374-80.), oligo-ligation assay (Grossman, P. D., et al. (1994) *Nucleic Acids Research* 22:4527-4534), locked nucleic acids (LNATM, Link, Technologies LTD, Lanarkshire, Scotland, EP patent 1013661, U.S. Pat. No. 6,268,490), Invader Assay (Aclara Biosciences, Wilkinson, D. (1999) *The Scientist* 13:16), padlock probes (Nilsson et al. *Science* (1994), 265: 2085), Sequence-tagged molecular inversion probes (similar to padlock probes) from ParAllele Bioscience (South San Francisco, Calif.; Hardenbol, P. et al. (2003) *Nature Biotechnology* 21:673-678), Molecular Beacons (Marras, S. A. et al. (1999 *Genet Anal.* 14:151-156), the READIT™ SNP Genotyping System from Promega (Madison, Wis.) (Rhodes R. B. et al. (2001) *Mol Diagn.* 6:55-61), Dynamic Allele-Specific Hybridization (DASH) (Prince, J. A. et al. (2001) Genome Research 11:152-162), the Qbead™ system (quantum dot encoded microspheres conjugated to allele-specific oligonucleotides) (Xu H. et al. (2003) *Nucleic Acids Research* 31:e43), Scorpion primers (similar to molecular beacons except unimolecular) (Thelwell, N. et al. (2000) *Nucleic Acids Research* 28:3752-3761), and Magiprobe (a novel fluorescence quenching-based oligonucleotide probe carrying a fluorophore and an intercalator) (Yamane A. (2002) *Nucleic Acids Research* 30:e97). In addition, Rae, K. V. N. et al. ((2003) *Nucleic Acids Research.* 31: e66), recently reported a microsphere-based genotyping assay that detects SNPs directly from human genomic DNA. The assay involves a structure-specific cleavage reaction, which generates fluorescent signal on the surface of microspheres, followed by flow cytometry of the microspheres. With a slightly different twist on the Sequenom technology (MALDI), Sauer et al. ((2003) *Nucleic Acids Research* 31:e63) generate charge-tagged DNA (post PCR and primer extension), using a photocleavable linker.

Accordingly, using the methods described above, the bovine haplotype allele or the nucleotide occurrence of a bovine SNP can be identified using an amplification reaction, a primer extension reaction, or an immunoassay. The bovine haplotype allele or bovine SNP can also be identified by contacting polynucleotides in the sample or polynucleotides derived from the sample, with a specific binding pair member that selectively hybridizes to a polynucleotide region comprising the bovine SNP, under conditions wherein the binding pair member specifically binds at or near the bovine SNP. The specific binding pair member can be an antibody or a polynucleotide.

The nucleotide occurrence of a SNP can be identified by other methodologies as well as those discussed above. For example, the identification can use microarray technology, which can be performed with PCR, for example using Affymetrix technologies and GenFlex Tag arrays (See e.g., Fan et al (2000) *Genome Res.* 10:853-860), or using a bovine gene chip containing proprietary SNP oligonucleotides (See e.g., Chee et al (1996), *Science* 274:610-614; and Kennedy et al. (2003) *Nature Biotech* 21:1233-1237) or without PCR, or sequencing methods such as mass spectrometry, scanning electron microscopy, or methods in which a polynucleotide flows past a sorting device that can detect the sequence of the polynucleotide. The occurrence of a SNP can be identified using electrochemical detection devices such as the eSensor™ DNA detection system (Motorola, Inc., Yu, C. J. (2001) *J. Am Chem. Soc.* 123:11155-11161). Other formats include melting curve analysis using fluorescently labeled hybridization probes, or intercalating dyes (Lohmann, S. (2000) *Biochemica* 4, 23-28, Herrmann, M. (2000) *Clinical Chemistry* 46: 425).

The SNP detection systems of the present invention typically utilize selective hybridization. As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying a nucleotide occurrence of a SNP. It will be recognized that some amount of non-specific hybridization is unavoidable, but is acceptable provide that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42 EC (moderate stringency conditions); and 0.1×SSC at about 68 EC (high stringency conditions).

Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 15 nucleotides in length, usually at least about 18 nucleotides, and particularly about 21 nucleotides or more in length.

A polynucleotide can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucleic Acids Research* (1994) 22:5220-5234 Jellinek et al., *Biochemistry* (1995) 34:11363-11372; Pagratis et al., *Nature Biotechnol.* (1997) 15:68-73, each of which is incorporated herein by reference). Primers and probes can also be comprised of peptide nucleic acids (PNA) (Nielsen P E and Egholm M. (1999) *Curr. Issues Mol. Biol.* 1:89-104).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* (1994) 22:977-986, Ecker and Crooke, *BioTechnology* (1995) 13:351360, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide or oligonucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). Thus, the term polynucleotide as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR).

In various embodiments for identifying nucleotide occurrences of SNPs, it can be useful to detectably label a polynucleotide or oligonucleotide. Detectable labeling of a polynucleotide or oligonucleotide is well known in the art. Particular non-limiting examples of detectable labels include chemiluminescent labels, fluorescent labels, radiolabels, enzymes, haptens, or even unique oligonucleotide sequences.

A method of the identifying a SNP also can be performed using a specific binding pair member. As used herein, the term "specific binding pair member" refers to a molecule that specifically binds or selectively hybridizes to another member of a specific binding pair. Specific binding pair member include, for example, probes, primers, polynucleotides, antibodies, etc. For example, a specific binding pair member includes a primer or a probe that selectively hybridizes to a target polynucleotide that includes a SNP loci or that hybridizes to an amplification product generated using the target polynucleotide as a template.

As used herein, the term "specific interaction," or "specifically binds" or the like means that two molecules form a complex that is relatively stable under physiologic conditions. The term is used herein in reference to various interactions, including, for example, the interaction of an antibody that binds a polynucleotide that includes a SNP site; or the interaction of an antibody that binds a polypeptide that includes an amino acid that is encoded by a codon that includes a SNP site. According to methods of the invention, an antibody can selectively bind to a polypeptide that includes a particular amino acid encoded by a codon that includes a SNP site. Alternatively, an antibody may preferentially bind a particular modified nucleotide that is incorporated into a SNP site for only certain nucleotide occurrences at the SNP site, for example using a primer extension assay.

A specific interaction can be characterized by a dissociation constant of at least about $1\times10^{-6}$ M, generally at least about $1\times10^{-7}$ M, usually at least about $1\times10^{-8}$ M, and particularly at least about $1\times10^{-9}$ M or $1\times10^{-10}$ M or less. A specific interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. Methods for determining whether two molecules interact specifically are well known and include, for example, equilibrium dialysis, surface plasmon resonance, and the like.

The invention also relates to kits, which can be used, for example, to perform a method of the invention. Thus, in one embodiment, the invention provides a kit for identifying nucleotide occurrences or haplotype alleles of bovine SNPs. Such a kit can contain, for example, an oligonucleotide probe, primer, or primer pair, or combinations thereof for identifying the nucleotide occurrence of at least one bovine single nucleotide polymorphism (SNP) associated with breed, such as a SNP corresponding to position 300 of any one of SEQ ID NOS:1 to 4868 or SEQ ID NOS:64887 to 64895. Such oligonucleotides being useful, for example, to identify a SNP or haplotype allele as disclosed herein; or can contain one or more polynucleotides corresponding to a portion of a bovine gene containing one or more nucleotide occurrences associated with a bovine trait, such polynucleotide being useful, for example, as a standard (control) that can be examined in parallel with a test sample. In addition, a kit of the invention can contain, for example, reagents for performing a method of the invention, including, for example, one or more detectable labels, which can be used to label a probe or primer or can be incorporated into a product generated using the probe or primer (e.g., an amplification product); one or more polymerases, which can be useful for a method that includes a primer extension or amplification procedure, or other enzyme or enzymes (e.g., a ligase or an endonuclease), which can be useful for performing an oligonucleotide ligation assay or a mismatch cleavage assay; and/or one or more buffers or other reagents that are necessary to or can facilitate performing a method of the invention. The primers or probes can be included in a kit in a labeled form, for example with a label such as biotin or an antibody. In one embodiment, a kit of the invention provides a plurality of oligonucleotides of the invention, including one or more oligonucleotide probes or one or more primers, including forward and/or reverse primers, or a combination of such probes and primers or primer pairs. Such a kit also can contain probes and/or primers that conveniently allow a method of the invention to be performed in a multiplex format.

The kit can also include instructions for using the probes or primers to determine a nucleotide occurrence of at least one bovine SNPs.

Population-specific alleles can be used to assign a bovine animal to a particular breed. These population specific alleles are fixed in the population of interest and absent in comparison populations. The absence of an allele in a sample of individuals from any one population may be because those alleles are truly population-specific or because the frequency of those alleles is low and the sample obtained from any given population was small (Taylor, J. F., Patent: PCT/US01/47521). For admixed populations, population-specific alleles rarely occur, however the difference in allele frequency between populations may still enable their use to infer assignment of individual bovines based to a breed, these are known as population associated alleles (Kumar, P., *Heredity* 91: 43-50 (2003)). Both population specific alleles and population-associated alleles are herein referred to as Breed-Specific Markers.

In the present invention, a marker is breed specific if it has a different allele frequency in one breed relative to one or more other breeds. A similar logic was employed by Kumar, P. (*Heredity* 91: 43-50 (2003)) to genetically distinguish cattle from European *Bos taurus* breeds and Indian *Bos indicus* breeds of cattle.

In the present invention there are 4868 breed-specific SNP markers. One or more of these markers could be used to determine breed specificity and/or to assign an individual to one or more breeds with an associated probability. These markers could be used alone or in any combination.

There are two broad classes of clustering methods that are used to assign individuals to populations (Pritchard, J. K., et al., *Genetics* 155: 945-959 (2000)). These are: 1) Distance-based methods: These calculate a pairwise distance matrix, whose entries give the distance between every pair of individuals. 2) Model-based methods: These proceed by assuming that observations from each cluster are random draws from some parametric model. Inference for the parameters corresponding to each cluster is then done jointly with inference for the cluster membership of each individual, using standard statistical methods. The preset disclosure includes the use of all standard statistical methods including maximum likelihood, bootstrapping methodologies, Bayesian methods and any other statistical methodology that can be employed to analyze such genome data. These statistical techniques are well known to those in the art.

Many software programs for molecular population genetics studies have been developed, their advantage lies in their pre-programmed complex mathematical techniques and ability to handle large volumes of data. Popular programs used by those in the field include, but are not limited to: TFPGA, Arlequin, GDA, GENEPOP, GeneStrut, POPGENE (Labate, J. A., *Crop Sci.* 40: 1521-1528. (2000)) and Structure. The present disclosure incorporates the use of all of the software disclosed above used to classify bovines into populations based on DNA polymorphisms as well as other software known in the art.

Structure has been used to determine population structure and infer assignment of individual animals to populations for livestock species including poultry (Rosenberg, N. A., et al., *Genetics.* 159: 699-713 (2001)) and bovines from South Asia (Kumar, P., *Heredity* 91: 43-50 (2003)).

As used herein, the term "hypermutable" refers to a nucleic acid sequence that is susceptible to instability, thus resulting in nucleic acid alterations. Such alterations include the deletion and addition of nucleotides. The hypermutable sequences of the invention are most often microsatellite DNA sequences which, by definition, are small tandem repeat DNA sequences. Thus, a combination of SNP analysis and microsatellite analysis may be used to infer a breed of a bovine subject.

The following examples are intended to illustrate but not limit the invention.

Example 1

Identification of SNPs that can be Used to Infer Breed

This example illustrates the use of whole genome shotgun sequencing and genotyping analysis to identify SNPs that can be used to infer breed of a bovine subject. Genomic DNA libraries were constructed from six breeds of cattle (Angus, Limousin, Brahman, Simmental, Holstein and Charolais). The libraries are a mixture of 2.5 and 10 kilobase inserts. Libraries from four of the cattle breeds (Angus, Brahman, Simmental and Limousin) were sequenced using the whole genome shotgun sequencing method developed by Celera Genomics (Venter, J. C. et al. (2001) *Science* 291:1304), to a depth of coverage sufficient to generate putative SNPs. The distribution of sequence fragments obtained from the cattle breeds was 32% Angus, 35% Limousin, 33% Brahman, and less than 1% Simmental. Upon whole genome assembly of the sequenced fragments, contigs were formed from consensus sequence, and sequence variants were identified and cataloged. 786,777 sequence variants that differed by a single nucleotide became candidate SNP markers for the high-density SNP map. The relative position of each candidate SNP within the bovine genome was determined using the assembled human genome as scaffolding, creating a candidate map of 242,181 human-mapped markers. Individual markers were tested to determine breed specificity within the cattle population using 196 animals representing diverse breeds (Angus, Charolais, Limousin, Hereford, Brahman, Simmental and Gelbvieh) and to ensure Mendelian segregation (20 trios of Beefmaster parents and progeny). The SNP detection platform used was the SNP-IT™ system (Beckman Coulter, Fullerton, Calif.). In general, SNP-IT™ is a 3-step primer extension reaction. In the first step a target polynucleotide is isolated from a sample by hybridization to a capture primer, which provide a first level of specificity. In a second step the capture primer is extended from a terminating nucleotide triphosphate at the target SNP site, which provides a second level of specificity. In a third step, the extended nucleotide trisphosphate can be detected using a variety of known formats, including, for example: direct fluorescence, indirect fluorescence, an indirect calorimetric assay, mass spectrometry, and fluorescence polarization. Reactions were processed in an automated 384 well format using a SNPstreaM™ instrument (Beckman Coulter, Fullerton, Calif.).

Allele frequencies within breed were determined using simple counting methods. Four thousand eight hundred and seventy seven breed specific markers (See SEQ ID NOS:1 to 4868 (Tables 5 and 6, filed herewith on a compact disc) and SEQ ID NOS:64887 to 64895 (Tables 3A and 3B)) were identified by analysis of over 19,000 markers tested. Details of the SNP markers that were identified as informative for breed, are listed in Tables 5 and 6 (filed herewith on a compact disc) and Tables 3A and 3B. Tables 3A and 5 provide the names of the identified SNP markers, breed specific alleles, their associated breed, allele frequencies, and breeds for which the alleles are most significantly associated (referred to as "major breeds" in the table). Tables 3B and 6 provide primer sequences (See "Forward," "Reverse," and "Extension") that were used to amplify a region that includes the SNP, and amplicon sequences that indicate the nucleotide occurrences for the SNP that were identified in brackets within the sequence.

Table 1 shows the number of SNP markers that had a non-zero allele frequency in the breed of interest. The fourth column shows the ability to distinguish a subpopulation from the total population as given by Wright's $F_{st}$ statistic. This statistic can take on a value of between 0 (meaning no ability to distinguish subpopulations [breeds] from the total population) and 1.0 meaning that different breeds can be identified perfectly. An $F_{st}$ value of zero means that a particular breed has the same allele frequency as the entire population (Weir, B. S. Genetic Data Analysis II. Methods for Discrete Population Genetic Data. Sinauer Associates, Sunderland, Mass. p 174. (1996)). Table 2 shows the number of SNP markers that were breed specific.

TABLE 1

Number of SNP markers per breed that have a non-zero allele frequency and ability to differentiate breeds from the whole population. Values for Wright's $F_{st}$ statistic are the mean of four replicates.

| Breed | Number of animals from that breed included in the analysis | Number of SNP markers per breed that have a non-zero allele frequency | Wright's $F_{st}$ statistic |
|---|---|---|---|
| Angus | 27 | 20 | .478 |
| Brahman | 27 | 24 | .553 |
| Charolais | 26 | 20 | .435 |
| Gelbvieh | 26 | 19 | .448 |
| Hereford | 26 | 10 | .622 |
| Limousin | 26 | 20 | .448 |
| Simmental | 26 | 20 | .411 |
| Beefmaster | 20 | | .343 |

TABLE 2

Number of Population Specific SNP markers per breed (i.e. at non-zero allele frequency in one breed and zero allele frequency in all other breeds)

| Breed | Number of Population Specific SNP markers per breed |
|---|---|
| Angus | 27 |
| Brahman | 2976 |
| Charolais | 2 |

TABLE 2-continued

Number of Population Specific SNP markers per breed (i.e. at non-zero allele frequency in one breed and zero allele frequency in all other breeds)

| Breed | Number of Population Specific SNP markers per breed |
|---|---|
| Gelbvieh | 3 |
| Hereford | 3 |
| Limousin | 20 |
| Simmental | 4 |

Example 2

Utilizing a Subset of Breed Specific Markers for Assigning Animals to the Correct Breed Category For this example, 48 SNP markers were selected from the 4868 markers identified to evaluate their efficacy for use in a breed specific panel. These 48 markers included MMBT05243, MMBT02545, MMBT14829, MMBT11932, MMBT23373, MBT08423, MMBT19771, MMBT10324, MMBT01611, MMBT08985, MMBT02110, MMBT17611, MMBT09623, MBT06416, MMBT04048, MMBT08023, MMBT11652, MMBT21228, MMBT12147, MMBT00059, MMBT21673, MBT09985, MMBT21682, MMBT06242, MMBT10530, MMBT06978, MMBT21426, MMBT21425, MMBT03692, MMBT11974, MMBT01651, MMBT01127, MMBT08438, MMBT03603, MMBT11644, MMBT14000, MMBT12659, MMBT21705, MMBT05684, MMBT21233, MMBT09242, MMBT09142, MMBT00761, MMBT02076, MMBT05710, MMBT21665, MMBT04130, and MMBT18672 (See Tables 3A and 3B below and Tables 5 and 6 (provided on a compact disc filed herewith)). Animals were assigned to a population based on their genetic profile of these 48 SNP markers using the software structure (Pritchard, J. K., et al., *Genetics* 155: 945-959 (2000)). One hundred and ninety six (196) animals were genotyped in the study from six *Bos taurus* breeds (Angus, Hereford, Simmental, Charolais, Limousin and Gelbvieh) and one *Bos indicus* (American Brahman) breed of cattle. One further breed (Beefmaster, an admixture of Brahman, Hereford and Shorthorn cattle) was included in the study—but Breed Specific Markers were not chosen specifically for this breed.

TABLE 3A

Allele Frequencies

| Marker | Breed Specific Allele | Breeds | AF1 | AF2 | AF3 | AF4 | Major Breeds |
|---|---|---|---|---|---|---|---|
| MMBT19771 | C | Angus Gelbvieh Hereford | 0.59 | 0.06 | 0.75 | | Angus, Hereford |
| MMBT08985 | A | Angus Charolais Gelbvieh Simmental | 0.74 | 0.05 | 0.04 | 0.2 | Angus, Simmental |
| MMBT21228 | T | Brahman Charolais Gelbvieh Limousin | 0.55 | 0.3 | 0.03 | 0.02 | Brahman, Charolais |
| MMBT12147 | C | Brahman Charolais Gelbvieh Simmental | 0.72 | 0.4 | 0.34 | 0.07 | Brahman Charolais Gelbvieh |
| MMBT00059 | G | Brahman Charolais Limousin Simmental | 0.82 | 0.28 | 0.04 | 0.19 | Brahman Charolais Gelbvieh |
| MMBT03692 | G | Angus Hereford Simmental | 0.11 | 0.38 | 0.07 | | Hereford Angus |
| MMBT01127 | C | Angus Brahman Charolais Hereford | 0.05 | 0.61 | 0.05 | 0.57 | Brahman Hereford |
| MMBT14000 | G | Limousin Simmental | 0.24 | 0.11 | | | Limousin |
| MMBT21665 | T | Brahman Charolais Limousin Simmental | 0.43 | 0.04 | 0.1 | 0.25 | Brahman Simmental |

TABLE 3B

Additional bovine SNPs associated with breed

| Markers | Forward | SEQ ID NOS: 64896-64904 | Reverse | SEQ ID NOS: 64905-64913 | Extension | SEQ ID NOS: 64914-64922 | Sequence | SEQ ID NOS: 64887-64895 |
|---|---|---|---|---|---|---|---|---|
| MMBT19771 | TAAATGGACCTTTGCTAAGTTTTG | 64896 | AGAACCACTTGGGGGTGG | 64905 | GGATGGCGTTCCGTCCTATTTACCCCACTCTCTGCTGTTGTCATG | 64914 | TCTAATTGTGTAATTTTCTGCAACTACTCTGGGACAAAAATCTTGGTAATTGGATTTTTTTAAACKAACAAGTTGTCACAATTGGATAGTTCTTAAACTATTTGTGCTTATGCTTCAGAAATTTTCAGTGGATGTACAGTGTATTTTAAATGTTTTGCATCAGCTTGTGGTCTCAAATTTGATTTAACTTTGAATTTTAAAATAGATTGACAACTCTGATTATACATTGTCTTCACTAAATGGACCTTTGCTAAGTTTTGAGTGTRTTCATCCCTACCCCACTCTCTGCTGTTGTCATG[C/G]GAGCTAAAATCCTGGCGGATTCAGCTCCACCCCCAAGTGGTTCGTCCCAGAGTGCTTTGCTGTTACTATGGAAATGCCTGCTTATTAATCTTGCTGTCCTTTTACTACCAAAGCACCTTTAACYGTCTCAAGCAATCAAGTGACGTTACCTACAGCAGGCAAAGGAAGAAGAAGACTGCTTCGCATCCTACAACTGCAATGCTGATTTAATCAAGATTTAATCAAGGAGCAGAAGGAACTAAAGCTACTCCAACAGCTCTTTAAAAATATACAAAGCTGGATCTTTCTGATGCAT | 64887 |

TABLE 3B-continued

Additional bovine SNPs associated with breed

| Markers | Forward | SEQ ID NOS: 64896-64904 | Reverse | SEQ ID NOS: 64905-64913 | Extension | SEQ ID NOS: 64914-64922 | Sequence | SEQ ID NOS: 64887-64895 |
|---|---|---|---|---|---|---|---|---|
| MMBT08985 | TTCTACTTCCCCCCTCTAATC | 64897 | AAAAAAGTCTTTAAAAAGATACGGG | 64906 | ACGCACGTCCACGGTGATTTGAAAAGAAACCCTTAGGTTTGGGGC | 64915 | CTCTGCACCCTGACTTTCCTGTCAAGTAGTTTATAATAACAGCTAACATTTATGGAGTGTTTGCAATGCACTGGGCTTCATGCCAAGCGCTTTACACACCTTGTCTTAATTAATCCTCCCAGCTACCCCCCAAGGTGTACATATCATTACCTCCACTCTCCTAGTGGAAACTGAGGCTCAGAGAAGCTAAGATCACCCCCCCTAGAAAGTGGCAGGGCCAGGATATGAAAACTGCGCTTAACCACCATGCTCTTCTACTTCCCCCCCTCTAATCTGAAAAGAAACCCTTAGGTTTGGGGC[A/T]TCTTTGTTTATAGACTGAAGCCCCGTATCTTTTTTAAAGACTTTTTTTGATGTGGATCATTTTTAAAGTCTTGATTGAATATGTTACAATATTGTTTCTGTTTAATGTTTTGGTTTTTTGGCCGTGAGACATGTTGGATGTCAGCTCCCCAGCGAGGGATCGAACCTGCACCCCCTGCAGGGTGAAGTCTCAGCCGCTGGACCACCAGGGAAGCCCCTGAAGGCCCCTATTGTAATGTGTATACTGTCCCCATGACTTAGATGCTTTGCAAGTTCAGATTTTTTATATTCTT TTGTTCAG | 64888 |
| MMBT21228 | ATGGGGTCATTCACTTGACTC | 64898 | ACACACCAAATCAGAGGTGAA | 64907 | AGATAGAGTCGATGCCAGCTTTCAGGCCTGTGACCACAGGCTCTT | 64916 | CTTCTTTCCCCCATTCCACGTGTAGGCACAGAGGCCTTTAAGCAGCACCACTTGTACCTGAGAAGCCCCAAGAAGCTGAGCTGGCAGGAGAGCTCCACCATCTGGTGCTAAAAAAAGTCCTGAGGTTCATAACCACCATCCGGTTCTTGGCCTTTACATAGCCACCTCTCGCTGAGGTCAGGGACCACTGAGCAGCGGCTGCTACCAGAAAACCACAGCCATTTCTCCCCATGGGGTCATTCACTTGACTCATGTGCTAATCATCTGCTCTGcATTCAGGCCTGTGACCACAGGCTCTT[G/T]MTAAGGTTGCCCAGGTGTCCTAGTCCTGACTTCACCTCTGATTTGGTGTGTGCCCTTCCCTAGCTGtTGCCTCCATATGTCCSTGTGGATGAAGCGGGGGTGCAGCGGGGGAGGGGGGGCTGTATGATTTGCGAGGGCTSTGCCATTCTGCTTCTCCCTGTGGAGGTGGTCTGTACCTAAAGGATGACCTCCAGAAAAAGCCCTGACACAACATGTATTTCCCTTCCCTTCTGAAATTGCTGACTTAAGACTCTTCCTCTTTGGCAAAGGTGCCAGGTAGCAGGCTCAGAGGCACAGATTC | 64889 |
| MMBT12147 | ACTGCACATAGCGGCCAT | 64899 | TCAGTACCAGTGACTGTAATCATGA | 64908 | AGGGTCTCTACGCTGACGATCTAATTACTATTACTTAATAAAAAA | 64917 | CATACATGCATGTGTGTGCAGTCACTTCAGTCATATCTGACTCTGTAATCCCATGGACTGTAGCCCACCAGTCTCCTCTGTCTACGAGATTTCCCAAGCAAGAATACTGGAGTGGGTTGCCATTTCCTCCTCCAGGAGATCTTCCCRACCTAGGGATTGAACTCACATCTCTTACAGCTCCTGCATTGGCAGACAGATACTTTACCACTGAGCCACCTGGGAAGCCCCCTACATTCCATACATATTTGGTTCAAACTGCACATAGCGGCCATTTCTAATTACTATTACTTAATAAAAAA[C/T]ACTTTTATAATTATGCATTAACTTCCCAATCATGATTACAGTCACTGGTACTGAGCAAGAACATTAAAAATCCAAGACTAGGCCCTGGAGTCCTGATTAGAATTGTACAGATAAACTTACAGGTTGGAGAGCAGACACAAGCCAAGTCTGTGTGCCATATTTTAATGGAAGTTTGCAGTAATCCATGCGAGAATGACCAATATTTCTCAAGTTCTTCTGGAACTAATGGTCTATTGCATTTTGTATTTAGAGTTATCCTAAATCATACATTTGGGGTATGCCAGTGCAAA TATAAAATGT | 64890 |
| MMBT00059 | TTCTCCCCCACAGAACCT | 64900 | ATTTGATTAGCTCACCTGTCAAC | 64909 | AGGGTCTCTACGCTGACGATAGTTGGCCTCAGAAACCTCAAGGAA | 64918 | TCCCTACCCCAGTACCTCAGAATGTGACTATACTTGGCCACAGGGTCTTTAAAGAGGTAACAGGGTAAAATAAGGTCATTAAGGTGAGCTCTAAGCCAAAACCTCTAAAGCGCTTATAAGAAGAGATGAGAACACAACCCACAGGTAACATACAGGGAGGAGGCCGCCTACGGCCAAGGAAAGACGTCTCCATCAAAGGAGATAAGGTTCGTAGGTCGGGAACACACACATGCTACTCTTCTCTGCTCCTGTGGTTCTCCCCCACAGAACCTTAAGTTGGCCTCAGAAACCTCAAGGAA[A/G]TACTTCAAGCTGCCACTATCAACCAACCAGGGTTGACAGGTGAGCTAATCAAATGACAGGAGAGCTTCCTGCTTCGATGCCCGGATGACCCACTGGGCTTCACTAAACCCCAGCTCCATGTGGACCCACTCCTTCCTGAGGCCTCCGTCTCCCCGTCCGTGAGACGCTGTCTACAGCCCTGCACGTACCTCCGTGAACTTGTCGGCCACCATGTAACGGACGCGCCAGGACTTGTCCTCAGCAGCCTGGCGCAGGGTGGGCATCACCAGGGCCTCCAGGTCCTCCTGGGGCAGGAGCTG | 64891 |

TABLE 3B-continued

Additional bovine SNPs associated with breed

| Markers | Forward | SEQ ID NOS: 64896- 64904 | Reverse | SEQ ID NOS: 64905- 64913 | Extension | SEQ ID NOS: 64914- 64922 | Sequence | SEQ ID NOS: 64887- 64895 |
|---|---|---|---|---|---|---|---|---|
| MMBT03692 | ACAAGAAG TAAAGGTG ATTGTTAG ACTA | 64901 | ATCTTGAAGG AATAGTTACT TTAAACACTT | 64910 | CGTGCCGCTCG TGATAGAATAA TTCTCTTATCT ATAAAAAGGAT T | 64919 | CTTCTCATGCAAGTAAGATAAACAGAAAATATTGTC TGAAGTTACTAATCCAGGTTTCATTGAATACCTTGT TTAGGTAGAGCAGAAAGTATGAAGAAAAAAAGACAA GTGTAATGGTCATACTCAATTCTAGTGTTTCTAATG ACTGAGTCAAATATGTAACAATTTATTTGTGTGTTT GTAATATTTTTAAAAGTTCATTCTGATGACCTTTCA ATATTCTTAAATTTATCAAGTCTAAGAGACAAGAAG TAAAGGTGATTGTTAGACTAATAATTCTCTTATCTA TAAAAAGGATT[A/G]TTTCCATGAGTTCATTCTCA TCTTTTAAGAAATGGAATATATTTTGAAGTGTTTAA AGTAACTATTCCTTCAAGATCACCCAAATCTACTCC TAATCACAATTTAATTAATTTTAGCTAACACATGAC TGGAGGTGTAGGTACTTAGATTATTCAAGTCTCCAC AGTCAGCCATGTTTTCCAGTGGCTGCTGATCATGAC ATCAGGCCCTGGTAAGACCTCCATTTTGGCCATTTT CATTATTGATGTAGGTTACATCAGACTAACAGTGGC TGAATATCAGCTGTTAGGCT GGCGAAGA | 64892 |
| MMBT01127 | TAGCTCTG TAAAAAGA ATATTATA ATGCTAAC | 64902 | TAAGTGCTGC TCTACCACAT G | 64911 | GCGGTAGGTTC CCGACATATCC AGTAACTATTA GTTGAAGAATA C | 64920 | GGGTTAAATGAGAGATTGGAGACAGCTTTGTAGCCT ATTGAAACAAAGTATGCCCTCAACAAACAGTTACTG ATTGATTGGTCAAGTCTATCAGACACTGGATACATT TAAAGCACATGATAAAAAAATGTACAGTTTTCTGAAT TTGTTATAAGTTCTGCTGAATCTGTCACATTTGATA AATTGGTCATAAATGACTATTATCTGTGAACATTTG TATGAATTCACCATGTTTTTATTTAGCTCTGTAAA AGAATATATTATAATGCTAACTGCCAGTAACTATTAG TTGAAGAATAC[A/C]TCCCTTTGAGCAGTTCAGTGC TTGGCATGTGGTAGAGCAGCACTTAGTAAGTGTTTG TTGAGTCAAAGAACAAATTATTAACAACTTCTAATC AAGGCCTTTGATTCTTCAGCAATTAAATCTCTTTAT TCTCATTTTTTACTTTATGGAGAAATGCTGACCAAT ATGATTTAAGTCACATACATAATTTTATGTTTTTCA GTATCCACGTTTGAAAAAGTAAAAGAAACAGCTGA AATTAATTTTAATAATGTATTTTATTTAASCCATGT CAATATATTATGGTTTTG ATATATAATC | 64893 |
| MMBT14000 | ACCGATGC TCACTGCT CA | 64903 | TTCTTTCGTC CGGGGTCG | 64912 | GGATGGCGTTC CGTCCTATTGT GCCCCGTTTAA AGCGGAGGAYT G | 64921 | AACTGTCCTGGGTTAGGGAATCCCTGAGCAATAGTC AATTAGGAACAGAGCGCTCGCCTCTAAGTTTAGTAC TGAGTCATCTGCAGACCCTGCTAAAGACGTGAAAAG ATAAAGGGTAGGAGAGCAAGGAGGGAGGGAGAGG AAGGGAGAGACGAGGGAAACAGGGACAGACACAGA GAAATATCCCTGGTCACCATCAACAGTTACGGAACT TCCCACAGTCCCACTCCCTCCACCGATGCTCACTGC TCAGGGCTGCCCTGAGGGTCACGTGCCCCGTTTAAA GCGGAGGAYTG[A/G]GGCTTCCAGAGGTGCCCGG ATCAGCCCGGCCGCCGCCAGCGCCCCKCAAGRGGGG GCCCGGATACGCCCGCGACCCCGGACGAAAGAAGCC TGCCCGCCCCCGGGCCCGCACACCTCCTCCTTCCG CGAGCGCTTGGACACTTTCTTCTCCATCTTAGCGGC CGTCTTCTCCGCCCCGCGGCCCTTCTTCTCTTTCTT GCCCTTTTTGCCCATCGCGCCGGATCCAAGGAGGCT TCTGARCCGCCTGTGAGACTCTAGCGGCGCGCCGCG CGCGGCGCGCAGGAAATACGTGCTgGGG | 64894 |
| MMBT21665 | TGTGGCAA ATGGCATA CG | 64904 | CATGTATGCG GATGGATGT | 64913 | AGAGCGAGTGA CGCATACTATT AGGCTTACTGT GGTGATGAGAC A | 64922 | TCTTTTTGCATTTATTCTTTTCTTCCCTTTTAAAAA ATAACTTTATTTATTTACTTATTTTTGTCTGCTAGG TCTGCATTGCTGCTCAGGCTTTTCCCCAGTTGTGGC AAGTGAGGGCTGTTCTCTGGTTTCAGGGTGGGCTTC TCACTGCCGTGGCTTCTCACTGCAGTGGCTTCTCGT GTGGAGTATGGGCCGTAGGGCACATGGGCTTTGGTA GTTACACCCTGGGGCTCTAGAGCACAYGCTCAATAT TTGTGGCAAATGGCATACGGGATCTTSTCAGATCAG GGATCAAACCC[A/G]TGTCTCATCACCACAGTAAG CCTAACATCCATCCGCATACATGGTTGCAATYATTT TTTCCTAGTGATGAGAACTTTTAAGATCTATTCTCT TGGCACGGCATTCTTAAAGTGCTTATTTTTCCACT TAAAAAAATCCAAGTTGGAAGCAGCATGTTATATT AAGAGATTCTGCATGTAATATGGGCATCTTAAATTT ACCATGAAACTGAATTTTTTGCCTTAGAGATGCAGA AGCTAGAATAATGGATATTATAATTCATGCTCAGTG ATGCTTCAGACAACAAATGTGACCTGTT | 64895 |

The number of populations K in the input file was eight. The value of K was chosen by sampling 100 SNP markers at random from the population and imputing a value of K from 4 to 12. The statistic In Pr(X|K) is the likelihood of the data given the assumed number of populations, where X is the genotypes of the sampled individuals and K is number of inferred populations (Rosenberg, N. A., et al., *Genetics*. 159: 699-713 (2001)). Three values of K, (K=7 to 9) gave the greatest likelihood of being the true number of populations in the study. The value of K=8 was chosen for future studies—the same number of known breeds in the population. The simulation was run with a burn in period of 25,000 iterations and a runtime of 100,000 iterations for four replicates. Input parameters included in the model are shown in Table 4.

TABLE 4

Parameters used in the model

| Number of SNP markers | n (number of animals) | B (number of breeds in input) | K (number of inferred populations) | Burn in period (iterations) | Run period (iterations) |
|---|---|---|---|---|---|
| 48 | 196 | 8 | 8 | 20,000 | 100,000 |

The structure program uses a model-based clustering method that employs a Markov Chain to estimate the posterior distribution (q) of each individual's admixture coefficient. The mean of this posterior distribution ($\hat{q}_k^{(i)}$) represents the mean of the proportion of an animal i's genome that is derived from a parental population (k) where $\Sigma_k q_k = 1$, i= 1, ... 196 animals and k=1, ... 7 breeds. The higher this value of $\hat{q}$, the greater the likelihood an animal is derived from a particular parental population k.

Table 7 shows the mean probability of assignment to a cluster for each of the eight breeds in the dataset. On average, animals from each breed were assigned to their own clusters with high probability for all of the pure-breeds represented (probability of cluster assignment ranged from 0.802 for Charolais to 0.949 for Brahman). The composite breed, Beefmaster had a lower probability of assignment to its own cluster (0.539) than the seven pure breeds but a significantly non-zero (0.269) probability of assignment to the Brahman cluster one of the parental breeds of Beefmaster. The results show that using genotype information alone, animals from the same breed were assigned to their respective population clusters with a high probability. Table 8 shows the mean individual admixture coefficient ($\hat{q}$) per animal as an estimate of probability each individual animal belonging to a particular cluster with K=8 different clusters.

TABLE 7

Probability of cluster assignment with 48 Breed-Specific SNP markers. Results are the mean of four replicate runs of structure.

| Breed | Cluster | | | | | | | |
|---|---|---|---|---|---|---|---|---|
| | 1 | 2 | 3 | 4 | 5 | 6 | 7 | 8 |
| Angus | .009 | .002 | .937 | .007 | .005 | .008 | .008 | .023 |
| Brahman | .005 | .949 | .020 | .004 | .003 | .006 | .006 | .008 |
| Charolais | .022 | .016 | .010 | .064 | .012 | .802 | .032 | .042 |
| Gelbvieh | .011 | .003 | .024 | .067 | .022 | .023 | .843 | .007 |
| Hereford | .948 | .002 | .004 | .008 | .004 | .007 | .022 | .005 |
| Limousin | .023 | .002 | .004 | .017 | .922 | .013 | .012 | .006 |
| Simmental | .008 | .003 | .006 | .924 | .024 | .013 | .016 | .006 |
| Beefmaster | .027 | .269 | .022 | .039 | .009 | .051 | .043 | .539 |

TABLE 8

Mean individual admixture coefficient ($\hat{q}$) per animal as an estimate of probability each individual animal belonging to a particular cluster with K = 8 different clusters.

| Breed of animal | Inferred population | | | | | | | |
|---|---|---|---|---|---|---|---|---|
| | 1 | 2 | 3 | 4 | 5 | 6 | 7 | 8 |
| Angus | 0.01 | 0.01 | 0.00 | 0.00 | 0.01 | 0.00 | 0.01 | 0.97 |
| Angus | 0.00 | 0.00 | 0.00 | 0.00 | 0.00 | 0.00 | 0.00 | 0.99 |
| Angus | 0.01 | 0.01 | 0.00 | 0.00 | 0.01 | 0.01 | 0.01 | 0.96 |
| Angus | 0.00 | 0.00 | 0.00 | 0.00 | 0.00 | 0.00 | 0.01 | 0.97 |
| Angus | 0.00 | 0.00 | 0.00 | 0.00 | 0.00 | 0.00 | 0.00 | 0.99 |
| Angus | 0.01 | 0.00 | 0.00 | 0.00 | 0.01 | 0.00 | 0.00 | 0.98 |
| Angus | 0.01 | 0.01 | 0.01 | 0.00 | 0.00 | 0.00 | 0.00 | 0.96 |
| Angus | 0.18 | 0.01 | 0.02 | 0.00 | 0.13 | 0.02 | 0.05 | 0.59 |
| Angus | 0.01 | 0.02 | 0.01 | 0.00 | 0.01 | 0.00 | 0.00 | 0.95 |
| Angus | 0.02 | 0.01 | 0.01 | 0.00 | 0.05 | 0.01 | 0.02 | 0.89 |
| Angus | 0.01 | 0.00 | 0.01 | 0.00 | 0.01 | 0.00 | 0.02 | 0.95 |
| Angus | 0.01 | 0.00 | 0.00 | 0.00 | 0.01 | 0.01 | 0.00 | 0.97 |
| Angus | 0.02 | 0.01 | 0.01 | 0.00 | 0.01 | 0.01 | 0.01 | 0.93 |
| Angus | 0.00 | 0.03 | 0.00 | 0.01 | 0.00 | 0.00 | 0.00 | 0.95 |
| Angus | 0.00 | 0.01 | 0.00 | 0.00 | 0.00 | 0.00 | 0.00 | 0.98 |
| Angus | 0.01 | 0.01 | 0.00 | 0.00 | 0.01 | 0.00 | 0.01 | 0.96 |
| Angus | 0.01 | 0.01 | 0.00 | 0.00 | 0.05 | 0.00 | 0.01 | 0.91 |
| Angus | 0.01 | 0.01 | 0.01 | 0.00 | 0.00 | 0.00 | 0.00 | 0.97 |
| Angus | 0.09 | 0.01 | 0.01 | 0.00 | 0.07 | 0.02 | 0.05 | 0.75 |
| Angus | 0.01 | 0.01 | 0.00 | 0.00 | 0.01 | 0.01 | 0.01 | 0.95 |
| Angus | 0.01 | 0.00 | 0.00 | 0.00 | 0.01 | 0.01 | 0.00 | 0.97 |
| Angus | 0.01 | 0.01 | 0.00 | 0.00 | 0.01 | 0.00 | 0.01 | 0.97 |
| Angus | 0.00 | 0.00 | 0.00 | 0.00 | 0.00 | 0.00 | 0.00 | 0.98 |
| Beefmaster | 0.02 | 0.01 | 0.24 | 0.42 | 0.16 | 0.01 | 0.13 | 0.03 |
| Beefmaster | 0.01 | 0.01 | 0.93 | 0.02 | 0.01 | 0.02 | 0.00 | 0.01 |
| Beefmaster | 0.01 | 0.02 | 0.91 | 0.06 | 0.01 | 0.00 | 0.00 | 0.00 |
| Beefmaster | 0.08 | 0.14 | 0.39 | 0.27 | 0.10 | 0.01 | 0.01 | 0.01 |
| Beefmaster | 0.03 | 0.24 | 0.06 | 0.63 | 0.02 | 0.01 | 0.01 | 0.00 |
| Beefmaster | 0.02 | 0.01 | 0.35 | 0.47 | 0.01 | 0.01 | 0.01 | 0.13 |
| Beefmaster | 0.24 | 0.11 | 0.14 | 0.45 | 0.02 | 0.01 | 0.03 | 0.01 |
| Beefmaster | 0.03 | 0.01 | 0.94 | 0.01 | 0.00 | 0.00 | 0.01 | 0.00 |
| Beefmaster | 0.07 | 0.01 | 0.81 | 0.02 | 0.04 | 0.01 | 0.01 | 0.03 |
| Beefmaster | 0.08 | 0.14 | 0.05 | 0.65 | 0.03 | 0.01 | 0.03 | 0.01 |
| Beefmaster | 0.04 | 0.01 | 0.06 | 0.67 | 0.05 | 0.01 | 0.14 | 0.02 |
| Beefmaster | 0.16 | 0.01 | 0.18 | 0.44 | 0.11 | 0.01 | 0.08 | 0.02 |
| Beefmaster | 0.01 | 0.00 | 0.98 | 0.00 | 0.00 | 0.00 | 0.00 | 0.00 |
| Beefmaster | 0.01 | 0.00 | 0.96 | 0.02 | 0.00 | 0.00 | 0.00 | 0.00 |
| Beefmaster | 0.36 | 0.01 | 0.59 | 0.01 | 0.02 | 0.01 | 0.01 | 0.00 |
| Beefmaster | 0.10 | 0.12 | 0.01 | 0.56 | 0.13 | 0.02 | 0.06 | 0.01 |
| Beefmaster | 0.01 | 0.00 | 0.96 | 0.00 | 0.01 | 0.00 | 0.01 | 0.01 |
| Beefmaster | 0.20 | 0.06 | 0.06 | 0.52 | 0.09 | 0.03 | 0.03 | 0.01 |
| Beefmaster | 0.17 | 0.05 | 0.24 | 0.43 | 0.03 | 0.01 | 0.02 | 0.05 |
| Beefmaster | 0.00 | 0.00 | 0.98 | 0.01 | 0.00 | 0.00 | 0.00 | 0.00 |
| Brahman | 0.00 | 0.00 | 0.02 | 0.96 | 0.01 | 0.00 | 0.00 | 0.00 |
| Brahman | 0.01 | 0.00 | 0.01 | 0.97 | 0.00 | 0.00 | 0.00 | 0.00 |
| Brahman | 0.01 | 0.00 | 0.02 | 0.94 | 0.01 | 0.01 | 0.01 | 0.01 |

TABLE 8-continued

Mean individual admixture coefficient ($\hat{q}$) per animal as an estimate of probability each individual animal belonging to a particular cluster with K = 8 different clusters.

| Breed of animal | Inferred population | | | | | | | |
|---|---|---|---|---|---|---|---|---|
| | 1 | 2 | 3 | 4 | 5 | 6 | 7 | 8 |
| Brahman | 0.01 | 0.04 | 0.01 | 0.92 | 0.01 | 0.01 | 0.01 | 0.00 |
| Brahman | 0.01 | 0.01 | 0.01 | 0.92 | 0.01 | 0.02 | 0.02 | 0.01 |
| Brahman | 0.01 | 0.01 | 0.01 | 0.97 | 0.01 | 0.00 | 0.01 | 0.00 |
| Brahman | 0.00 | 0.00 | 0.00 | 0.99 | 0.00 | 0.00 | 0.00 | 0.00 |
| Brahman | 0.01 | 0.01 | 0.00 | 0.96 | 0.01 | 0.01 | 0.01 | 0.00 |
| Brahman | 0.00 | 0.00 | 0.00 | 0.98 | 0.00 | 0.00 | 0.00 | 0.00 |
| Brahman | 0.05 | 0.00 | 0.03 | 0.85 | 0.02 | 0.01 | 0.01 | 0.04 |
| Brahman | 0.00 | 0.00 | 0.00 | 0.98 | 0.00 | 0.00 | 0.00 | 0.00 |
| Brahman | 0.00 | 0.00 | 0.00 | 0.98 | 0.00 | 0.00 | 0.00 | 0.00 |
| Brahman | 0.01 | 0.01 | 0.02 | 0.94 | 0.01 | 0.01 | 0.01 | 0.00 |
| Brahman | 0.00 | 0.00 | 0.01 | 0.98 | 0.00 | 0.00 | 0.00 | 0.00 |
| Brahman | 0.00 | 0.00 | 0.01 | 0.98 | 0.00 | 0.00 | 0.00 | 0.00 |
| Brahman | 0.00 | 0.00 | 0.01 | 0.98 | 0.00 | 0.00 | 0.00 | 0.00 |
| Brahman | 0.00 | 0.00 | 0.00 | 0.99 | 0.00 | 0.00 | 0.00 | 0.00 |
| Brahman | 0.00 | 0.00 | 0.01 | 0.97 | 0.00 | 0.00 | 0.00 | 0.01 |
| Brahman | 0.00 | 0.00 | 0.01 | 0.97 | 0.01 | 0.00 | 0.00 | 0.00 |
| Brahman | 0.00 | 0.01 | 0.00 | 0.98 | 0.00 | 0.00 | 0.00 | 0.00 |
| Brahman | 0.00 | 0.00 | 0.00 | 0.99 | 0.00 | 0.00 | 0.00 | 0.00 |
| Brahman | 0.00 | 0.00 | 0.00 | 0.98 | 0.00 | 0.00 | 0.00 | 0.00 |
| Brahman | 0.00 | 0.00 | 0.00 | 0.98 | 0.00 | 0.00 | 0.00 | 0.00 |
| Brahman | 0.00 | 0.00 | 0.00 | 0.99 | 0.00 | 0.00 | 0.00 | 0.00 |
| Brahman | 0.00 | 0.00 | 0.00 | 0.99 | 0.00 | 0.00 | 0.00 | 0.00 |
| Brahman | 0.02 | 0.00 | 0.03 | 0.89 | 0.02 | 0.01 | 0.02 | 0.01 |
| Charolais | 0.84 | 0.01 | 0.02 | 0.02 | 0.03 | 0.01 | 0.06 | 0.03 |
| Charolais | 0.38 | 0.01 | 0.15 | 0.01 | 0.13 | 0.00 | 0.13 | 0.19 |
| Charolais | 0.03 | 0.02 | 0.89 | 0.00 | 0.02 | 0.01 | 0.02 | 0.01 |
| Charolais | 0.72 | 0.00 | 0.01 | 0.01 | 0.24 | 0.01 | 0.01 | 0.00 |
| Charolais | 0.74 | 0.01 | 0.16 | 0.01 | 0.02 | 0.04 | 0.01 | 0.01 |
| Charolais | 0.97 | 0.00 | 0.01 | 0.00 | 0.01 | 0.00 | 0.00 | 0.00 |
| Charolais | 0.96 | 0.01 | 0.01 | 0.00 | 0.01 | 0.01 | 0.00 | 0.00 |
| Charolais | 0.96 | 0.00 | 0.01 | 0.00 | 0.02 | 0.00 | 0.01 | 0.00 |
| Charolais | 0.97 | 0.00 | 0.01 | 0.00 | 0.01 | 0.01 | 0.01 | 0.00 |
| Charolais | 0.92 | 0.04 | 0.02 | 0.02 | 0.01 | 0.00 | 0.00 | 0.00 |
| Charolais | 0.88 | 0.00 | 0.01 | 0.00 | 0.01 | 0.01 | 0.08 | 0.00 |
| Charolais | 0.67 | 0.02 | 0.12 | 0.00 | 0.15 | 0.01 | 0.02 | 0.02 |
| Charolais | 0.96 | 0.00 | 0.01 | 0.00 | 0.01 | 0.01 | 0.01 | 0.00 |
| Charolais | 0.97 | 0.00 | 0.01 | 0.00 | 0.01 | 0.01 | 0.01 | 0.00 |
| Charolais | 0.68 | 0.01 | 0.02 | 0.00 | 0.03 | 0.01 | 0.25 | 0.00 |
| Charolais | 0.96 | 0.01 | 0.01 | 0.00 | 0.01 | 0.01 | 0.01 | 0.00 |
| Charolais | 0.14 | 0.01 | 0.01 | 0.00 | 0.83 | 0.01 | 0.01 | 0.00 |
| Charolais | 0.96 | 0.00 | 0.00 | 0.00 | 0.01 | 0.01 | 0.02 | 0.00 |
| Charolais | 0.97 | 0.00 | 0.00 | 0.00 | 0.01 | 0.00 | 0.01 | 0.00 |
| Charolais | 0.95 | 0.01 | 0.00 | 0.01 | 0.01 | 0.01 | 0.01 | 0.00 |
| Charolais | 0.95 | 0.01 | 0.01 | 0.00 | 0.01 | 0.00 | 0.01 | 0.00 |
| Charolais | 0.96 | 0.01 | 0.01 | 0.00 | 0.01 | 0.00 | 0.01 | 0.00 |
| Charolais | 0.94 | 0.01 | 0.01 | 0.00 | 0.02 | 0.01 | 0.02 | 0.00 |
| Charolais | 0.90 | 0.05 | 0.01 | 0.00 | 0.01 | 0.01 | 0.01 | 0.00 |
| Charolais | 0.96 | 0.01 | 0.01 | 0.00 | 0.01 | 0.01 | 0.01 | 0.00 |
| Charolais | 0.95 | 0.00 | 0.01 | 0.00 | 0.03 | 0.01 | 0.01 | 0.00 |
| Gelbvieh | 0.05 | 0.01 | 0.01 | 0.00 | 0.93 | 0.00 | 0.01 | 0.00 |
| Gelbvieh | 0.01 | 0.00 | 0.01 | 0.05 | 0.77 | 0.01 | 0.13 | 0.03 |
| Gelbvieh | 0.01 | 0.00 | 0.00 | 0.00 | 0.96 | 0.01 | 0.01 | 0.00 |
| Gelbvieh | 0.01 | 0.01 | 0.00 | 0.00 | 0.97 | 0.00 | 0.01 | 0.00 |
| Gelbvieh | 0.01 | 0.01 | 0.00 | 0.00 | 0.96 | 0.01 | 0.01 | 0.00 |
| Gelbvieh | 0.01 | 0.00 | 0.00 | 0.00 | 0.95 | 0.03 | 0.01 | 0.00 |
| Gelbvieh | 0.01 | 0.01 | 0.00 | 0.00 | 0.95 | 0.01 | 0.02 | 0.00 |
| Gelbvieh | 0.05 | 0.06 | 0.09 | 0.00 | 0.64 | 0.01 | 0.01 | 0.14 |
| Gelbvieh | 0.15 | 0.01 | 0.01 | 0.00 | 0.79 | 0.01 | 0.03 | 0.01 |
| Gelbvieh | 0.01 | 0.01 | 0.00 | 0.00 | 0.96 | 0.01 | 0.01 | 0.00 |
| Gelbvieh | 0.06 | 0.01 | 0.01 | 0.00 | 0.86 | 0.01 | 0.04 | 0.01 |
| Gelbvieh | 0.01 | 0.00 | 0.01 | 0.00 | 0.66 | 0.01 | 0.02 | 0.29 |
| Gelbvieh | 0.01 | 0.00 | 0.00 | 0.00 | 0.76 | 0.17 | 0.05 | 0.00 |
| Gelbvieh | 0.01 | 0.01 | 0.01 | 0.00 | 0.51 | 0.01 | 0.46 | 0.00 |
| Gelbvieh | 0.01 | 0.01 | 0.00 | 0.00 | 0.97 | 0.01 | 0.00 | 0.00 |
| Gelbvieh | 0.00 | 0.00 | 0.00 | 0.00 | 0.97 | 0.01 | 0.00 | 0.00 |
| Gelbvieh | 0.01 | 0.00 | 0.00 | 0.00 | 0.96 | 0.01 | 0.01 | 0.00 |
| Gelbvieh | 0.01 | 0.02 | 0.01 | 0.00 | 0.32 | 0.02 | 0.61 | 0.02 |
| Gelbvieh | 0.00 | 0.00 | 0.01 | 0.00 | 0.98 | 0.00 | 0.00 | 0.00 |
| Gelbvieh | 0.01 | 0.00 | 0.01 | 0.00 | 0.92 | 0.01 | 0.04 | 0.00 |
| Gelbvieh | 0.03 | 0.00 | 0.01 | 0.00 | 0.94 | 0.01 | 0.01 | 0.01 |
| Gelbvieh | 0.00 | 0.00 | 0.00 | 0.00 | 0.98 | 0.00 | 0.00 | 0.00 |
| Gelbvieh | 0.02 | 0.00 | 0.01 | 0.00 | 0.89 | 0.01 | 0.07 | 0.00 |
| Gelbvieh | 0.01 | 0.01 | 0.00 | 0.00 | 0.96 | 0.01 | 0.01 | 0.00 |
| Gelbvieh | 0.01 | 0.00 | 0.00 | 0.00 | 0.88 | 0.06 | 0.05 | 0.00 |
| Hereford | 0.01 | 0.95 | 0.01 | 0.00 | 0.01 | 0.01 | 0.01 | 0.01 |
| Hereford | 0.01 | 0.98 | 0.00 | 0.00 | 0.00 | 0.00 | 0.00 | 0.00 |
| Hereford | 0.01 | 0.97 | 0.00 | 0.00 | 0.01 | 0.00 | 0.00 | 0.00 |
| Hereford | 0.01 | 0.97 | 0.01 | 0.00 | 0.01 | 0.00 | 0.01 | 0.00 |
| Hereford | 0.01 | 0.93 | 0.02 | 0.00 | 0.01 | 0.00 | 0.01 | 0.04 |
| Hereford | 0.02 | 0.94 | 0.01 | 0.00 | 0.01 | 0.01 | 0.01 | 0.01 |
| Hereford | 0.01 | 0.97 | 0.00 | 0.00 | 0.01 | 0.00 | 0.01 | 0.00 |
| Hereford | 0.00 | 0.98 | 0.00 | 0.00 | 0.00 | 0.00 | 0.00 | 0.00 |
| Hereford | 0.09 | 0.77 | 0.01 | 0.00 | 0.07 | 0.02 | 0.04 | 0.01 |
| Hereford | 0.01 | 0.98 | 0.00 | 0.00 | 0.01 | 0.00 | 0.00 | 0.00 |
| Hereford | 0.00 | 0.98 | 0.00 | 0.00 | 0.00 | 0.00 | 0.00 | 0.00 |
| Hereford | 0.00 | 0.98 | 0.00 | 0.00 | 0.00 | 0.00 | 0.00 | 0.00 |
| Hereford | 0.01 | 0.97 | 0.00 | 0.00 | 0.01 | 0.00 | 0.00 | 0.00 |
| Hereford | 0.41 | 0.16 | 0.03 | 0.00 | 0.36 | 0.01 | 0.03 | 0.01 |
| Hereford | 0.00 | 0.99 | 0.00 | 0.00 | 0.00 | 0.00 | 0.00 | 0.00 |
| Hereford | 0.01 | 0.98 | 0.00 | 0.00 | 0.01 | 0.00 | 0.00 | 0.00 |
| Hereford | 0.12 | 0.74 | 0.01 | 0.00 | 0.08 | 0.02 | 0.03 | 0.01 |
| Hereford | 0.01 | 0.98 | 0.00 | 0.00 | 0.01 | 0.00 | 0.00 | 0.00 |
| Hereford | 0.01 | 0.97 | 0.00 | 0.00 | 0.01 | 0.00 | 0.01 | 0.00 |
| Hereford | 0.00 | 0.95 | 0.00 | 0.00 | 0.00 | 0.01 | 0.00 | 0.03 |
| Hereford | 0.01 | 0.97 | 0.00 | 0.00 | 0.01 | 0.00 | 0.01 | 0.00 |
| Hereford | 0.00 | 0.99 | 0.00 | 0.00 | 0.00 | 0.00 | 0.00 | 0.00 |
| Hereford | 0.03 | 0.91 | 0.01 | 0.00 | 0.02 | 0.01 | 0.01 | 0.01 |
| Hereford | 0.00 | 0.99 | 0.00 | 0.00 | 0.00 | 0.00 | 0.00 | 0.00 |
| Hereford | 0.01 | 0.96 | 0.01 | 0.00 | 0.01 | 0.01 | 0.01 | 0.00 |
| Hereford | 0.01 | 0.97 | 0.01 | 0.00 | 0.01 | 0.00 | 0.01 | 0.00 |
| Limousin | 0.01 | 0.01 | 0.01 | 0.00 | 0.01 | 0.97 | 0.01 | 0.00 |
| Limousin | 0.01 | 0.01 | 0.01 | 0.00 | 0.03 | 0.92 | 0.02 | 0.00 |
| Limousin | 0.01 | 0.00 | 0.01 | 0.00 | 0.01 | 0.97 | 0.01 | 0.00 |
| Limousin | 0.02 | 0.00 | 0.01 | 0.00 | 0.07 | 0.89 | 0.01 | 0.01 |
| Limousin | 0.01 | 0.00 | 0.00 | 0.00 | 0.01 | 0.97 | 0.01 | 0.00 |
| Limousin | 0.01 | 0.00 | 0.00 | 0.00 | 0.00 | 0.98 | 0.01 | 0.00 |
| Limousin | 0.01 | 0.00 | 0.00 | 0.00 | 0.01 | 0.95 | 0.02 | 0.00 |
| Limousin | 0.01 | 0.01 | 0.00 | 0.00 | 0.01 | 0.96 | 0.01 | 0.00 |
| Limousin | 0.02 | 0.01 | 0.01 | 0.00 | 0.01 | 0.94 | 0.01 | 0.02 |
| Limousin | 0.01 | 0.00 | 0.00 | 0.00 | 0.01 | 0.97 | 0.01 | 0.00 |
| Limousin | 0.02 | 0.02 | 0.02 | 0.00 | 0.05 | 0.86 | 0.04 | 0.01 |
| Limousin | 0.01 | 0.00 | 0.00 | 0.00 | 0.00 | 0.97 | 0.01 | 0.01 |
| Limousin | 0.01 | 0.00 | 0.00 | 0.00 | 0.01 | 0.97 | 0.01 | 0.00 |
| Limousin | 0.09 | 0.05 | 0.01 | 0.00 | 0.18 | 0.56 | 0.10 | 0.01 |
| Limousin | 0.29 | 0.01 | 0.01 | 0.00 | 0.01 | 0.67 | 0.01 | 0.00 |
| Limousin | 0.01 | 0.00 | 0.00 | 0.00 | 0.01 | 0.96 | 0.01 | 0.00 |
| Limousin | 0.00 | 0.00 | 0.00 | 0.00 | 0.01 | 0.97 | 0.01 | 0.01 |
| Limousin | 0.00 | 0.00 | 0.00 | 0.00 | 0.01 | 0.98 | 0.01 | 0.00 |
| Limousin | 0.14 | 0.00 | 0.02 | 0.01 | 0.01 | 0.80 | 0.03 | 0.00 |
| Limousin | 0.04 | 0.00 | 0.00 | 0.00 | 0.01 | 0.90 | 0.05 | 0.00 |
| Limousin | 0.00 | 0.00 | 0.00 | 0.00 | 0.00 | 0.98 | 0.00 | 0.00 |
| Limousin | 0.01 | 0.00 | 0.00 | 0.00 | 0.01 | 0.97 | 0.01 | 0.00 |
| Limousin | 0.00 | 0.00 | 0.03 | 0.00 | 0.00 | 0.93 | 0.03 | 0.00 |
| Limousin | 0.03 | 0.01 | 0.01 | 0.00 | 0.02 | 0.92 | 0.01 | 0.00 |
| Limousin | 0.01 | 0.01 | 0.09 | 0.00 | 0.01 | 0.69 | 0.18 | 0.00 |
| Limousin | 0.00 | 0.00 | 0.00 | 0.00 | 0.00 | 0.99 | 0.00 | 0.00 |
| Simmental | 0.35 | 0.02 | 0.01 | 0.00 | 0.15 | 0.01 | 0.45 | 0.01 |
| Simmental | 0.01 | 0.00 | 0.00 | 0.00 | 0.01 | 0.00 | 0.97 | 0.00 |
| Simmental | 0.01 | 0.00 | 0.00 | 0.00 | 0.01 | 0.00 | 0.96 | 0.01 |
| Simmental | 0.02 | 0.01 | 0.01 | 0.00 | 0.01 | 0.02 | 0.94 | 0.01 |
| Simmental | 0.22 | 0.01 | 0.01 | 0.00 | 0.09 | 0.01 | 0.66 | 0.01 |
| Simmental | 0.01 | 0.00 | 0.00 | 0.00 | 0.01 | 0.01 | 0.97 | 0.00 |
| Simmental | 0.02 | 0.00 | 0.01 | 0.00 | 0.49 | 0.00 | 0.48 | 0.00 |
| Simmental | 0.01 | 0.00 | 0.00 | 0.00 | 0.01 | 0.01 | 0.96 | 0.01 |
| Simmental | 0.02 | 0.01 | 0.00 | 0.00 | 0.02 | 0.01 | 0.90 | 0.04 |
| Simmental | 0.01 | 0.00 | 0.01 | 0.00 | 0.01 | 0.01 | 0.95 | 0.01 |
| Simmental | 0.02 | 0.00 | 0.01 | 0.01 | 0.01 | 0.01 | 0.95 | 0.00 |
| Simmental | 0.00 | 0.00 | 0.00 | 0.00 | 0.01 | 0.00 | 0.98 | 0.00 |
| Simmental | 0.00 | 0.11 | 0.00 | 0.00 | 0.01 | 0.00 | 0.87 | 0.00 |
| Simmental | 0.02 | 0.01 | 0.01 | 0.00 | 0.02 | 0.37 | 0.57 | 0.01 |
| Simmental | 0.01 | 0.00 | 0.01 | 0.00 | 0.00 | 0.01 | 0.97 | 0.00 |
| Simmental | 0.02 | 0.00 | 0.01 | 0.00 | 0.01 | 0.06 | 0.90 | 0.00 |
| Simmental | 0.01 | 0.00 | 0.03 | 0.00 | 0.02 | 0.01 | 0.93 | 0.00 |
| Simmental | 0.01 | 0.00 | 0.00 | 0.00 | 0.03 | 0.00 | 0.93 | 0.02 |

TABLE 8-continued

Mean individual admixture coefficient (q̂) per animal as an estimate of probability each individual animal belonging to a particular cluster with K = 8 different clusters.

| Breed of animal | Inferred population | | | | | | | |
|---|---|---|---|---|---|---|---|---|
| | 1 | 2 | 3 | 4 | 5 | 6 | 7 | 8 |
| Simmental | 0.05 | 0.02 | 0.01 | 0.04 | 0.01 | 0.01 | 0.86 | 0.01 |
| Simmental | 0.03 | 0.01 | 0.03 | 0.00 | 0.02 | 0.01 | 0.91 | 0.00 |
| Simmental | 0.01 | 0.00 | 0.00 | 0.00 | 0.01 | 0.00 | 0.97 | 0.00 |
| Simmental | 0.01 | 0.00 | 0.00 | 0.00 | 0.01 | 0.01 | 0.96 | 0.00 |
| Simmental | 0.02 | 0.00 | 0.00 | 0.00 | 0.10 | 0.38 | 0.48 | 0.00 |
| Simmental | 0.01 | 0.01 | 0.01 | 0.00 | 0.01 | 0.04 | 0.92 | 0.00 |

Example 3

Identification of Angus Vs Non-Angus

In another aspect of the invention, 12 SNP markers were selected and tested for their ability to distinguish Angus from non-Angus breeds. These markers included MMBT05243, MMBT02545, MMBT14829, MMBT1932, MMBT23373, MBT08423, MMBT19771, MMBT10324, MMBT01611, MMBT08985, MMBT02110, and MMBT17611 (See Tables 5 and 6). Parameters used in this analysis are shown in Table 9.

TABLE 9

Parameters used in the model

| Number of SNP markers | n (number of animals) | B (number of breeds in input) | K (number of inferred populations) | Burn in period (iterations) | Run period (iterations) |
|---|---|---|---|---|---|
| 12 | 196 | 8 | 2 (Angus and non-Angus) | 50,000 | 250,000 |

The mean individual admixture coefficient (q̂) for Angus and non-Angus animals was 0.968 and 0.924, respectively, indicating a very high probability of assigning an animal from one of these populations to the correct cluster. The mean individual admixture coefficient (q̂) per animal is shown in Table 10.

TABLE 10

Mean individual admixture coefficient (q̂) per animal as an estimate of probability each individual animal belongs to a particular cluster.

| Breed of animal | Inferred population | |
|---|---|---|
| | 1 | 2 |
| Angus | 0.99 | 0.02 |
| Angus | 1.00 | 0.00 |
| Angus | 0.98 | 0.02 |
| Angus | 0.99 | 0.01 |
| Angus | 1.00 | 0.01 |
| Angus | 0.99 | 0.01 |
| Angus | 0.99 | 0.01 |
| Angus | 0.40 | 0.60 |
| Angus | 0.98 | 0.02 |
| Angus | 0.88 | 0.12 |
| Angus | 0.98 | 0.02 |
| Angus | 0.98 | 0.02 |
| Angus | 0.95 | 0.05 |
| Angus | 0.99 | 0.01 |
| Angus | 0.99 | 0.01 |
| Angus | 0.97 | 0.03 |
| Angus | 0.95 | 0.05 |
| Angus | 0.99 | 0.01 |
| Angus | 0.46 | 0.54 |
| Angus | 0.95 | 0.05 |
| Angus | 0.97 | 0.03 |
| Angus | 0.98 | 0.02 |
| Angus | 0.99 | 0.01 |
| non Angus | 0.02 | 0.98 |
| non Angus | 0.02 | 0.99 |
| non Angus | 0.02 | 0.98 |
| non Angus | 0.01 | 0.99 |
| non Angus | 0.02 | 0.98 |
| non Angus | 0.02 | 0.99 |
| non Angus | 0.01 | 0.99 |
| non Angus | 0.02 | 0.99 |
| non Angus | 0.01 | 0.99 |
| non Angus | 0.08 | 0.92 |
| non Angus | 0.31 | 0.69 |
| non Angus | 0.01 | 0.99 |
| non Angus | 0.02 | 0.98 |
| non Angus | 0.02 | 0.98 |
| non Angus | 0.04 | 0.97 |
| non Angus | 0.01 | 0.99 |
| non Angus | 0.02 | 0.98 |
| non Angus | 0.04 | 0.96 |
| non Angus | 0.17 | 0.83 |
| non Angus | 0.01 | 0.99 |
| non Angus | 0.01 | 0.99 |
| non Angus | 0.04 | 0.96 |
| non Angus | 0.01 | 0.99 |
| non Angus | 0.01 | 0.99 |
| non Angus | 0.02 | 0.98 |
| non Angus | 0.04 | 0.96 |
| non Angus | 0.01 | 0.99 |
| non Angus | 0.01 | 0.99 |
| non Angus | 0.58 | 0.42 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 1.00 |

TABLE 10-continued

Mean individual admixture coefficient (q̂) per animal as an estimate of probability each individual animal belongs to a particular cluster.

| Breed of animal | Inferred population | |
|---|---|---|
| | 1 | 2 |
| non Angus | 0.01 | 1.00 |
| non Angus | 0.01 | 0.99 |
| non Angus | 0.01 | 1.00 |
| non Angus | 0.01 | 0.99 |
| non Angus | 0.01 | 1.00 |
| non Angus | 0.01 | 0.99 |
| non Angus | 0.01 | 1.00 |
| non Angus | 0.01 | 0.99 |
| non Angus | 0.01 | 1.00 |
| non Angus | 0.01 | 1.00 |
| non Angus | 0.01 | 1.00 |
| non Angus | 0.01 | 1.00 |
| non Angus | 0.01 | 0.99 |
| non Angus | 0.01 | 0.99 |
| non Angus | 0.01 | 0.99 |
| non Angus | 0.01 | 1.00 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 1.00 |
| non Angus | 0.01 | 0.99 |
| non Angus | 0.33 | 0.67 |
| non Angus | 0.01 | 1.00 |
| non Angus | 0.01 | 1.00 |
| non Angus | 0.01 | 0.99 |
| non Angus | 0.01 | 1.00 |
| non Angus | 0.01 | 1.00 |
| non Angus | 0.34 | 0.66 |
| non Angus | 0.01 | 0.99 |
| non Angus | 0.01 | 1.00 |
| non Angus | 0.01 | 0.99 |
| non Angus | 0.01 | 1.00 |
| non Angus | 0.01 | 1.00 |
| non Angus | 0.01 | 1.00 |
| non Angus | 0.01 | 0.99 |
| non Angus | 0.01 | 0.99 |
| non Angus | 0.01 | 0.99 |
| non Angus | 0.01 | 0.99 |
| non Angus | 0.05 | 0.95 |
| non Angus | 0.01 | 0.99 |
| non Angus | 0.02 | 0.99 |
| non Angus | 0.01 | 0.99 |
| non Angus | 0.01 | 1.00 |
| non Angus | 0.01 | 0.99 |
| non Angus | 0.02 | 0.98 |
| non Angus | 0.02 | 0.99 |
| non Angus | 0.01 | 0.99 |
| non Angus | 0.01 | 1.00 |
| non Angus | 0.01 | 0.99 |
| non Angus | 0.01 | 0.99 |
| non Angus | 0.01 | 1.00 |
| non Angus | 0.01 | 0.99 |
| non Angus | 0.01 | 0.99 |
| non Angus | 0.16 | 0.85 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 1.00 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 0.99 |
| non Angus | 0.01 | 1.00 |
| non Angus | 0.01 | 0.99 |
| non Angus | 0.01 | 0.99 |
| non Angus | 0.17 | 0.83 |
| non Angus | 0.01 | 0.99 |
| non Angus | 0.01 | 0.99 |
| non Angus | 0.08 | 0.92 |
| non Angus | 0.01 | 0.99 |
| non Angus | 0.01 | 0.99 |
| non Angus | 0.01 | 0.99 |
| non Angus | 0.01 | 1.00 |
| non Angus | 0.07 | 0.93 |
| non Angus | 0.01 | 0.99 |
| non Angus | 0.01 | 0.99 |
| non Angus | 0.01 | 1.00 |
| non Angus | 0.01 | 1.00 |
| non Angus | 0.01 | 1.00 |
| non Angus | 0.01 | 0.99 |
| non Angus | 0.01 | 1.00 |
| non Angus | 0.01 | 0.99 |
| non Angus | 0.01 | 1.00 |
| non Angus | 0.01 | 0.99 |
| non Angus | 0.40 | 0.60 |
| non Angus | 0.02 | 0.98 |
| non Angus | 0.01 | 0.99 |
| non Angus | 0.01 | 0.99 |
| non Angus | 0.01 | 0.99 |
| non Angus | 0.01 | 0.99 |
| non Angus | 0.26 | 0.74 |
| non Angus | 0.10 | 0.91 |
| non Angus | 0.02 | 0.98 |
| non Angus | 0.01 | 0.99 |
| non Angus | 0.26 | 0.74 |
| non Angus | 0.01 | 0.99 |
| non Angus | 0.01 | 0.99 |
| non Angus | 0.02 | 0.98 |
| non Angus | 0.01 | 1.00 |
| non Angus | 0.01 | 1.00 |
| non Angus | 0.42 | 0.59 |
| non Angus | 0.01 | 0.99 |
| non Angus | 0.01 | 1.00 |
| non Angus | 0.01 | 1.00 |
| non Angus | 0.01 | 1.00 |
| non Angus | 0.01 | 1.00 |
| non Angus | 0.01 | 1.00 |
| non Angus | 0.09 | 0.91 |
| non Angus | 0.01 | 0.99 |
| non Angus | 0.01 | 0.99 |
| non Angus | 0.01 | 0.99 |
| non Angus | 0.01 | 0.99 |
| non Angus | 0.28 | 0.73 |
| non Angus | 0.01 | 0.99 |
| non Angus | 0.01 | 0.99 |
| non Angus | 0.10 | 0.90 |
| non Angus | 0.01 | 0.99 |
| non Angus | 0.05 | 0.95 |
| non Angus | 0.01 | 0.99 |
| non Angus | 0.02 | 0.98 |
| non Angus | 0.02 | 0.98 |
| non Angus | 0.01 | 1.00 |
| non Angus | 0.01 | 0.99 |
| non Angus | 0.02 | 0.98 |
| non Angus | 0.01 | 0.99 |
| non Angus | 0.05 | 0.96 |
| non Angus | 0.03 | 0.98 |

This tool can be used to identify the percentage of each breed comprising an individual animal. These data can be used to manage feedlot cattle for specific growth and development traits. In one aspect, cattle identified from the exotic breed type (Charolais, Gelbvieh, Limousin, and Simmental) have high growth rate and large harvest sizes. These cattle can be managed to maximize growth rate and lean meat yield. Cattle identified as English type (Angus and Hereford) produce high quality meat products and can be marketed into the high quality yield grade. Breed specified products can certify that the product is in fact from the breed labeled.

Although the invention has been described with reference to the above example, it will be understood that modifications and variations are encompassed within the spirit and scope of the invention. Accordingly, the invention is limited only by the following claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08026064B2). An electronic copy of the "Sequence Listing" will also be available from the USPTO upon request and payment of the fee set forth in 37 CFR 1.19(b)(3).

---

What is claimed is:

1. A method to identify a breed of a bovine subject comprising amplifying a nucleic acid sample of the bovine subject, and identifying in the amplified nucleic acid sample, at least two single nucleotide polymorphisms (SNPs) in more than one gene, wherein the SNPs are associated with a breed, thereby identifying the breed of the bovine subject.

2. The method of claim 1, wherein the nucleotide occurrence of the at least 2 SNPs comprise a haplotype allele, and wherein the method infers the breed using the identified haplotype allele.

3. The method of claim 2, further comprising identifying a diploid pair of haplotype alleles and inferring the breed using the diploid pair of haplotype alleles.

4. The method of claim 1, further comprising marketing the subject prior to harvest based on the inferred breed.

5. The method of claim 1, further comprising managing the subject in the feedlot to obtain improved performance based on known characteristics of the inferred breed for the subject.

6. The method of claim 1, further comprising identifying a nucleotide sequence of a hypermutable sequence in the sample, and inferring breed based on the at least one nucleotide occurrence and the nucleotide sequence of the hypermutable sequence.

7. The method of claim 1, further comprising marketing a product of the bovine subject on the inferred breed.

8. The method of claim 7, wherein the marketing of the product comprises marketing the product under a trademark specific for a breed.

9. The method of claim 1, wherein occurrences of at least five single nucleotide polymorphisms (SNPs) are identified.

10. The method of claim 1, wherein occurrences of at least seven single nucleotide polymorphisms (SNPs) are identified.

11. The method of claim 1, wherein occurrences of at least ten single nucleotide polymorphisms (SNPs) are identified.

12. The method of claim 1, wherein the at least two SNPs occur in more than a single gene.

13. The method of claim 1, wherein at least one SNP occurs in a non-coding region of the genome.

14. The method of claim 1 wherein the breed is Angus.

15. The method of claim 1 wherein the breed is Holstein.

16. The method of claim 1 wherein the breed is Limousin.

17. The method of claim 1 wherein the breed is Brahman.

18. The method of claim 1 wherein the breed is Simmental.

19. The method of claim 1 wherein the breed is Hereford.

20. The method of claim 1 wherein the breed is Gelbvieh.

21. The method of claim 1 wherein the breed is Charolais.

22. The method of claim 1 wherein the breed is identified using allele frequencies of the SNPs associated with the breed.

23. The method of claim 1 wherein the method further comprising comprises using multi-locus haplotypes that are associated with a breed.

24. The method of claim 1 wherein the method comprises using microsequencing techniques to identify the at least 2 SNPs.

25. The method of claim 1 wherein the method distinguishes a bovine subject as Angus or non-Angus.

26. The method of claim 1 wherein the method comprises using population-specific alleles and population-associated alleles.

* * * * *